United States Patent [19]

Amano et al.

[11] Patent Number: 4,835,707
[45] Date of Patent: May 30, 1989

[54] AUTOMATIC ANALYSIS METHOD AND APPARATUS FOR ENZYME REACTION

[75] Inventors: Toshio Amano, Takatsuki; Isuke Imada, Izumi, both of Japan

[73] Assignee: Takeda Chemical Industries, Ltd., Osaka, Japan

[21] Appl. No.: 76,720

[22] Filed: Jul. 22, 1987

[30] Foreign Application Priority Data

| Jul. 23, 1986 | [JP] | Japan | 61-174515 |
| Jul. 23, 1986 | [JP] | Japan | 61-174516 |
| Jul. 23, 1986 | [JP] | Japan | 61-174517 |
| Jul. 23, 1986 | [JP] | Japan | 61-174518 |

[51] Int. Cl.$^4$ .................... G06F 15/42; G01N 1/00
[52] U.S. Cl. .................... 364/497; 73/863.01; 73/863.25; 364/500; 364/513; 422/62; 422/67
[58] Field of Search ............ 364/496, 497, 500, 513, 364/413; 73/863.01, 863.25, 863.32, 864.81; 422/62, 67

[56] References Cited

U.S. PATENT DOCUMENTS

| 3,960,003 | 6/1976 | Beyer et al. | 73/61.1 C |
| 4,063,077 | 12/1977 | Wright | 364/497 |
| 4,158,545 | 6/1979 | Yamashita et al. | 364/497 |
| 4,224,405 | 9/1980 | Hiaikata | 364/497 |
| 4,271,123 | 6/1981 | Curry et al. | 364/497 |
| 4,281,387 | 7/1981 | Kraft et al. | 364/497 |
| 4,335,438 | 6/1982 | Smolen | 364/497 |
| 4,459,265 | 7/1984 | Berglund | 364/497 |
| 4,483,927 | 11/1984 | Takekawa | 364/497 |
| 4,539,645 | 9/1985 | Krottinger et al. | 73/863.01 |
| 4,558,421 | 12/1985 | Shriver | 364/513 |
| 4,578,764 | 3/1986 | Hutchins et al. | 364/513 |
| 4,633,413 | 12/1986 | Caveney et al. | 364/500 |
| 4,647,432 | 3/1987 | Wakatake | 73/863.32 |
| 4,689,755 | 8/1987 | Buote | 364/513 |
| 4,698,766 | 10/1987 | Entwistle et al. | 364/513 |

FOREIGN PATENT DOCUMENTS

2491215 9/1980 France.

OTHER PUBLICATIONS

International Lab, vol. 12, No. 7 (9/82); "Robotic Approach to Automated Sample Preparation"; G. L. Hawke et al.; pp. 48–56.
Trends in Analy. Chem., vol. 4, No. 2 (2/85); "Robots in Flexible Analysis Systems"; P. Koole et al.; pp. 44–49.
Analy. Chem., vol. 48, No. 4 (4/76); "Automated Computer-Controlled Solution Handling System . . . "; B. W. Renoe et al.; pp. 661–666.
Analy. Chem., vol. 44, No. 12 (10/72); "Automated Reaction-Rate Methods of Analysis"; H. V. Malmstadt et al.; pp. 26A–41A.

Primary Examiner—Parshotam S. Lall
Assistant Examiner—Kevin J. Teska
Attorney, Agent, or Firm—Wenderoth, Lind & Ponack

[57] ABSTRACT

An automatic analysis method of and apparatus for the full automation of an enzyme reaction analysis from the pretreatment step of the reaction to the data processing step, wherein the operation of the pretreatment step is arranged to be sequentially performed on many samples with full automation by the use of robots and computers to improve savings efficiency and measurement accuracy. Also, the pretreatment steps of weighing samples in many sample tubes, adding the given amount of solvent corresponding to the weighing value and placing the samples into the dissolution vessel to dissolve the sample in the solvent are adapted to be sequentially performed with full automation with the use of the robot, computer and electronic balance. Furthermore, the filtration, concentration and the injecting operations into the HPLC are automatically performed. The automatic apparatuses are coupled to each other so that the filtration, concentration, injecting operations are allowed to be sequentially performed with full automation using an on-line system.

22 Claims, 26 Drawing Sheets

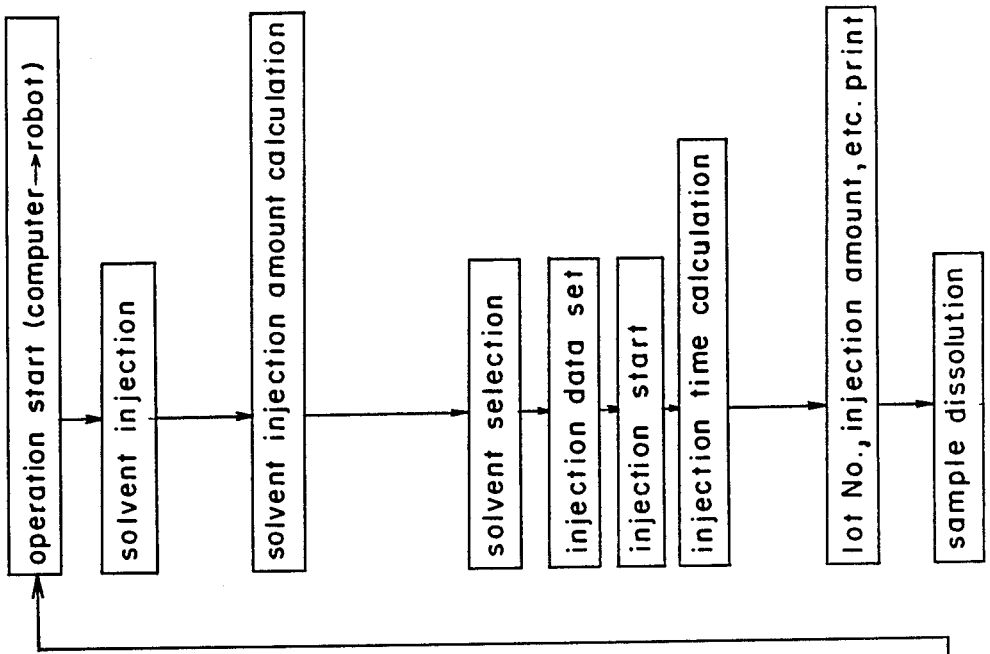
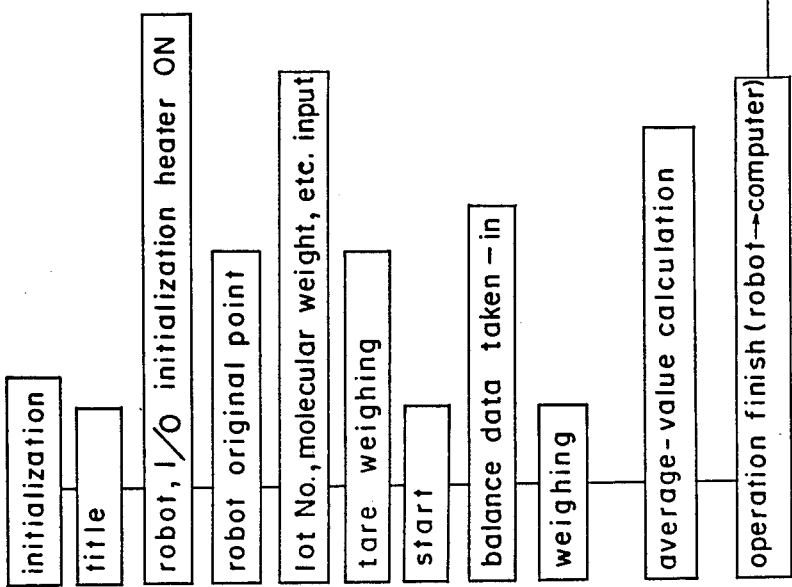
Fig. 9

Fig. 10
Fig. 10(A)
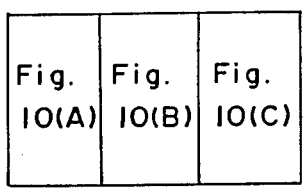
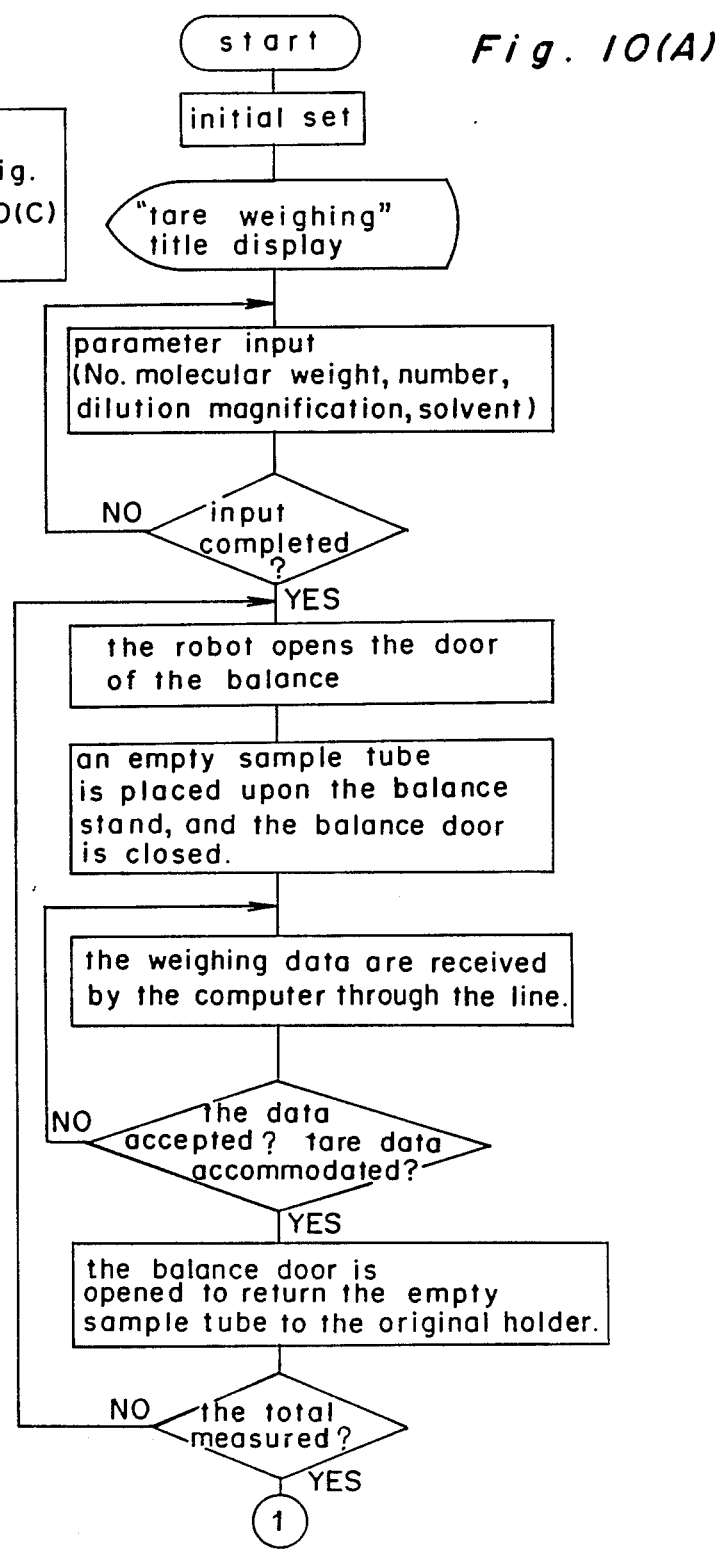

remark

1.: 15-HETE
2.: 11-HETE
3 : 8-, 12-HETE
4.: 9-HETE
5 : 5-HETE remark $\begin{pmatrix} 1 : 15\text{-HETE} \\ 2 : 11\text{-HETE} \\ 3 : 8\text{-},12\text{-HETE} \\ 4 : 9\text{-HETE} \\ 5 : 5\text{-HETE} \end{pmatrix}$

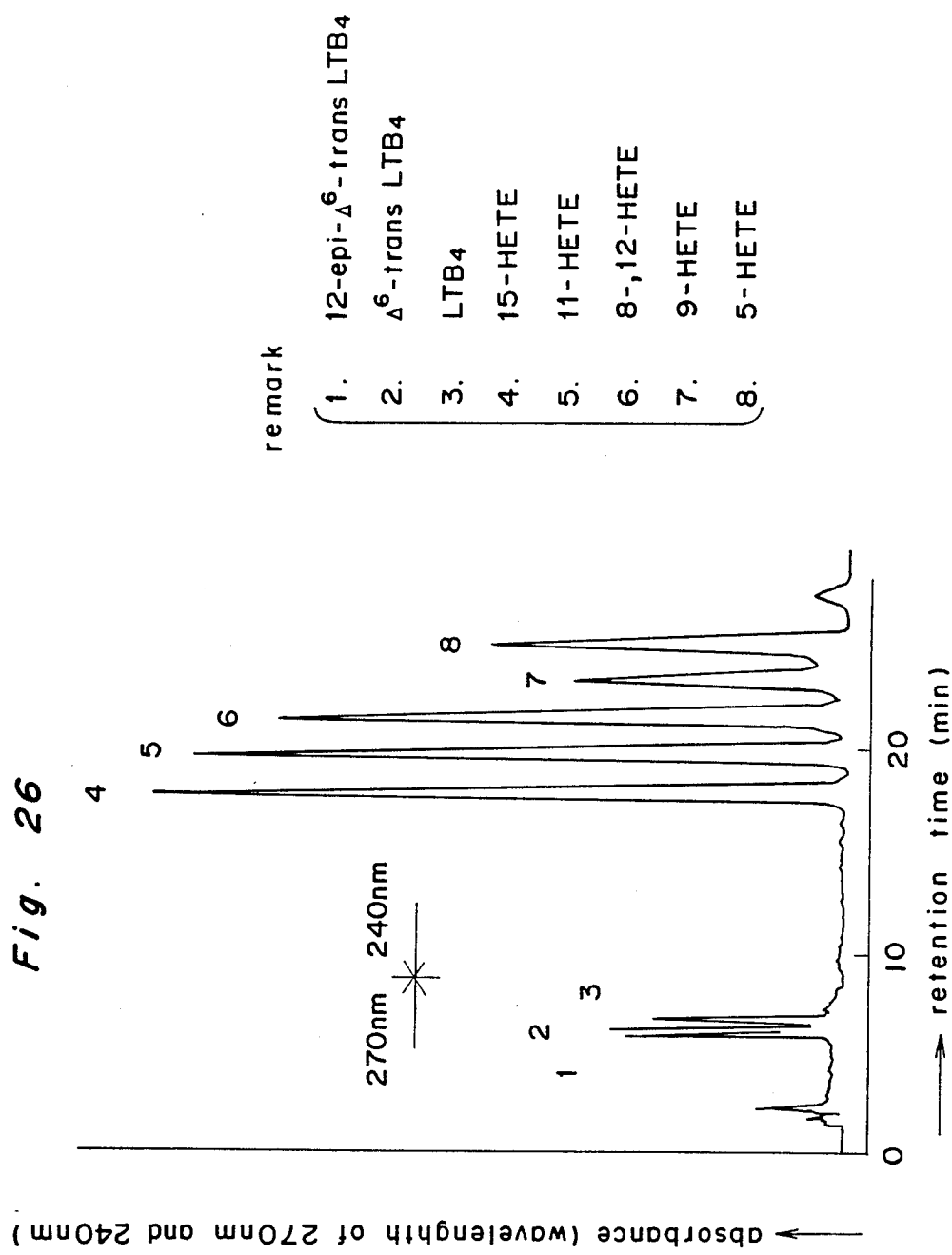

AUTOMATIC ANALYSIS METHOD AND APPARATUS FOR ENZYME REACTION

BACKGROUND OF THE INVENTION

The present invention relates to an automatic analysis method for an enzyme reaction and an apparatus thereof, and, more particularly, to a method and an apparatus for the full automation of an enzyme reaction analysis. In particular, the present invention provided an automatic analysis system where an assay of the effects of substances on the lipoxygenase and cyclooxygenase enzyme systems in the arachidonic acid cascade is performed with respect to various compounds with the minimum labor necessary through use of measurement automation in order to provide data for the selection of a secondary screening compound.

In the biochemistry field, it is extremely important to analyze the effects of various materials on an enzyme reaction for the primary screening of a biologically-active substance and the elucidation of the reaction mechanism thereof. Particularly, to identify an active substance, it is necessary to analyze the effects of many substances on a constant enzyme reaction.

Generally, the automatic analytical system (which is called "Laboauto") is divided into steps of pretreatment of the sample, analysis and data processing/analysis. Conventionally, use of laboratory automation is introduced in the analysis and the data processing/analysis steps, but since the pretreatment step is complicated and contains various methods, it is often introduced.

Thus, the operations required to be carried out in the pretreatment step, for example, weighing, dissolution, dilution, reaction, filtration, concentration and injection into the analytical apparatus, are performed by the manual method. As these operations are complicated, many problems result such that more time is required, efficiency is deteriorated, and analytical precision is lowered, thus resulting in poor measurement accuracy.

SUMMARY OF THE INVENTION

Accordingly, in the present invention, all operations of the pretreatment step are adapted to be sequentially performed on many samples with full automation by the use of robots, computers and so on to improve savings, efficiency and measurement accuracy.

The present invention provides an apparatus for elucidating the physiological and pharmacological roles of useful, minor-tissue components such as arachidonic acid metabolites, their influence upon pathologic physiology, and for screening substances regulating their metabolism. In particular, the present invention provides a method of and an apparatus for observing and controlling the operations of an analysis, e.g., the weighing, dissolution, dilution, and pipetting of a sample using robots as well as the operations of, filtration, concentration, and injection, utilizing an incubator, a preservation vessel, a high performance liquid chromatograph (HPLC) and an automatic data processing apparatus.

The operations of the pretreatment step, e.g. weighing samples, adding a given amount of solvent to a sample corresponding to the weighing value, and placing the sample and solvent into a dissolution vessel to dissolve the sample, are sequentially performed with full automation with the use of a first robot, a computer and an electronic balance, thus resulting in improved savings, efficiency and measurement accuracy.

In addition, according to the present invention, the pretreatment step is automated using a second robot, wherein the sample dilution, the sampling of the diluted sample into a reaction tube and the pipetting of the reaction mixture are also automated. Hence, the whole analysis system including the pretreatment step is fully automated to improve savings, efficiency and analytical precision.

Furthermore, the operations of filtration, concentration and injection of a sample into the HPLC are automated, in that the automatic apparatuses are coupled to each other so that the filtration, concentration, and injection operations are sequentially performed with full automation using a continuous on-line system to improve savings, efficiency and measurement accuracy.

To achieve the above-described object, the present invention provides a method and an apparatus for performing sequentially and automatically the weighing operation of a sample, the adding operation of solvent to the sample, the dissolving operation of the sample in the solvent, the adding operation of solvent to the sample solution, the pipetting operation of the diluted sample solution into a reaction tube, the adding operation of enzymes into the reaction tube, the moving operation of the reaction tube into a preservation vessel, the filtering operation of the reaction mixture in the reaction tube to get a filtrate, the concentrating operation of the filtrate, and the pipetting operation of the concentrated filtrate into an analysis apparatus.

More particularly, the present invention provides for the following: with a weighing and dissolution apparatus, grasping a sample tube retained in a rack with a chuck provided on a movable arm of a first automatic robot for weighing the sample with an electronic balance, adding a predetermined amount of solvent to the sample in accordance with the weighing value of the sample, placing the sample tube into the dissolution vessel to dissolve the sample after the addition of solvent, moving the sample tube containing the dissolved sample onto a rack for dilution provided on a dilution and reacting apparatus; with the dilution and reacting apparatus, grasping a nozzle of a dilution dispenser, a sampling pipetter or an enzyme reaction mixture dispenser with the chuck of a second automatic robot to move the nozzle into the sample tube retained on the dilution rack or the reaction tube retained on a rack in an incubator, adding the diluted solution from the dilution dispenser into the sample tube located in the dilution rack to perform the diluting operation by a given amount, taking a sampling of the diluted solution from the sample tube with the sampling pipetter to inject it into the reaction tube, sequentially injecting enzymes and factors necessary for the enzyme reaction into the reaction tube at intervals of a given time, grasping the reaction tube with the second robot to move it into the preservation vessel after the reaction; grasping the reaction tube retained in the preservation vessel with the second robot to place it in the position of a reaction mixture sampling needle disposed in a filtration, concentration and analysis apparatus, filtering the reaction mixture through a filtration unit after the sampling operation of reaction mixture with the sampling needle, feeding eluate into a concentration column after adsorption of the filtrate onto the concentration column, automatically injecting it into an analysis column for analysis by a HPLC, processing the obtained data by a data processing apparatus; and automatically controlling the operations of the first and second robots in accordance with a program input into a computer to automatically perform all of the operations from weighing to analysis.

Also, in the above-described enzyme reaction automatic analysis apparatus, the automatic weighing and dissolution apparatus comprises a rack for retaining many sample tubes, an electronic balance, a solvent dispenser. and a dissolution vessel with an ultrasonicator thereon, all disposed at different positions on the periphery of the robot, so that the sample tube retained in the rack is grasped with a chunk disposed on a movable arm of the robot and moved to the electronic balance, the solvent adding apparatus, and the dissolution vessel.

The dilution and reacting apparatus comprises a dilution rack for retaining many sample tubes, an incubator provided with a rack for retaining many reaction tubes, a dilution dispenser, a sampling pipetter, a plurality of dispensers for injecting enzymes, and a preservation vessel provided with a rack for retaining the reaction tubes, all disposed at different positions on the periphery of the second robot, so that the nozzle of each dispenser is grasped with the chuck of the robot and moved to the sample tube or reaction tube to perform the injection, and so that the reaction tube in the incubator is grasped with the chuck of the robot and moved onto the rack of the preservation vessel.

The filtration/concentration/injection apparatus (FCI) comprises a sampling nozzle for taking a sampling of the reaction mixture from the reaction tube through the operation of a syringe pump, a filtration unit of a filter paper continuous winding type for filtering the sampling reaction mixture, a concentration column for concentrating the filtrate, and a valve for feeding the eluate into the concentration column whereby it is automatically injected into the analysis column, so that each of these apparatuses is so disposed that the filtration, concentration, and injection operations may be performed using a continuous on-line system.

Although any enzyme may be used in the present invention, an enzyme showing biological activity is preferable with the substrate of the enzyme or the product of the reaction being extremely small in amount. For example, the lipoxygenase or the cyclooxygenase enzymes are preferable with the products being leukotrienes, prostaglandins and thromboxanes. As for the enzyme preparation, tissue cells or cell lines can be used in addition to purified enzymes. For example, soy bean lipoxygenase refined from the soy bean is used. Rat basophilic leukemia cell (RBL-1), procine or rat platelets are also used.

As described hereinabove, the enzyme reaction starts with the addition of substrate and factors necessary for the enzyme reaction to a solution containing a sample or only solvent. The enzyme reaction is stopped by the addition of an organic solvent or by a reduction in temperature. The analysis of the enzyme, reaction mixture is performed by the HPLC. The enzyme reaction mixture is filtered, concentrated by a constant amount, and the obtained concentrated solution is injected into the HPLC apparatus for analysis. The results of the analysis show an inhibition or acceleration of the enzyme reaction as compared with a control where only solvent is added.

Also, to achieve the above-described object, the present invention provides an automatic weighing and dissolution apparatus for samples, comprising a rack for retaining a plurality of sample tubes which are freely removable for performing operations in the different positions on the periphery of the first automatic robot, an electronic balance, solvent adding apparatuses, a dissolution vessel with an ultrasonicator on it, so that the sample tube in the rack into which the sample is deposited is freely grasped with a chuck disposed on a movable arm of the first automatic robot and moved sequentially and automatically to the electronic balance, solvent adding apparatus and the dissolution vessel. Moreover, there is provided a computer for controlling the operation of the robot, for setting the amount of solvent to add which amount is calculated in accordance with the weight of the sample for adding the solvent into the sample tube, and for automatically controlling each of the apparatuses such as the dissolution vessel into which the sample tube after the addition of the solvent is placed.

Furthermore, in order to achieve the above-described object, the present invention provides an automatic dilution and reacting apparatus which comprises a rack for retaining a plurality of sample tubes, a dilution dispenser, a sampling pipetter, an incubator having a plurality of reaction tubes disposed in it, reaction mixture dispensers, and a nozzle washing vessel, all disposed on different positions on the periphery of the second automatic robot. Also provided are nozzles mounted through flexible pipes on each of the dispensers, the nozzles being detachably placed on nozzle stands provided in the operation range of the robot, so that each of the nozzles is freely grasped with a chuck provided on a movable arm of the robot and inserted into the opening of the sample tube in the rack or into the opening of a reaction tube in the incubator. Additionally, the robot is operated by a controller to inject the solvent into the sample tube in the rack from the dilution dispenser, whereupon the diluted sample is pipetted from the sample tube by the sampling pipetter and injected into the reaction tube within the incubator, after which the reaction mixture components, such as cells as the enzyme solution, arachidonic acid, and ethanol are sequentially added at intervals of a given time from the reaction mixture dispensers into the diluted sample located within the incubator for the reacting operation.

Furthermore, to achieve the above-described object, the present invention uses an on-line filtration system, instead of the conventional centrifugal separation system, to remove the admixture of protein or the like. A system for continuously winding the filter paper which is simpler and more inexpensive is used in the apparatus as the filtration system, i.e., a system of having a band-shaped filter paper is placed on the passage, taken up after the filtration and replaced with new paper. Also, in the concentration operation, the present system adopts a concentration method using a precolumn, because a reversed phase HPLC is used in the identification and estimation of the sample. Namely, a preliminary column (concentration column) of a small size for absorbing the sample is disposed before an analysis column, and the sample is dissolved in solvent which is higher in polarity than the eluate. When it is moved through the column, the sample is absorbed. Then it is continuously guided into the analysis column from the concentration column with the eluate, so the concentration may be performed by the on-line system at the same time as the separation and estimation of the sample. When a sample of 1 m is injected into the concentration column, a sensibility increase of 20 through 50 times is caused in the injection amount (20 through 50μ) in the conventional HPLC. Also, the filtration apparatus is coupled to the concentration apparatus, to which an HPLC injecting apparatus with a six-way valve switch is mounted, which apparatuses together become the FCI. Hence, the series of operations for filtration concentration injection into the HPLC may be automatically effected by the apparatus.

Specifically, the present invention provides the FCI, which is also provided with a sampling nozzle for taking a sampling of the sample solution from the sample tube, a syringe pump for operating the sampling nozzle, a filtration unit for filtering the sampled sample solution using the filter-paper continuous winding type, a six-way valve with a sampling loop on it to which the filtered sample solution is passed, a six-way valve with a concentration column on it, and a water pump which feeds the sample solution in the loop of the six-way valve with a sampling loop together with water into the concentration column of the six-way valve with the concentration column.

BRIEF DESCRIPTION OF THE DRAWINGS

These and other objects and features of the present invention will become apparatus from the following description taken in conjunction with the preferred embodiment thereof with reference to the accompanying drawings, in which:

FIG. 9 is a block diagram showing the operation sequence of the apparatus of FIG. 1;

FIGS. 10, 10(A), 10(B) and 10(C) are flow charts showing the operation sequence;

FIG. 26 shows a chromatogram obtained by using the conventional method;

DETAILED DESCRIPTION OF THE INVENTION

Figure 1:
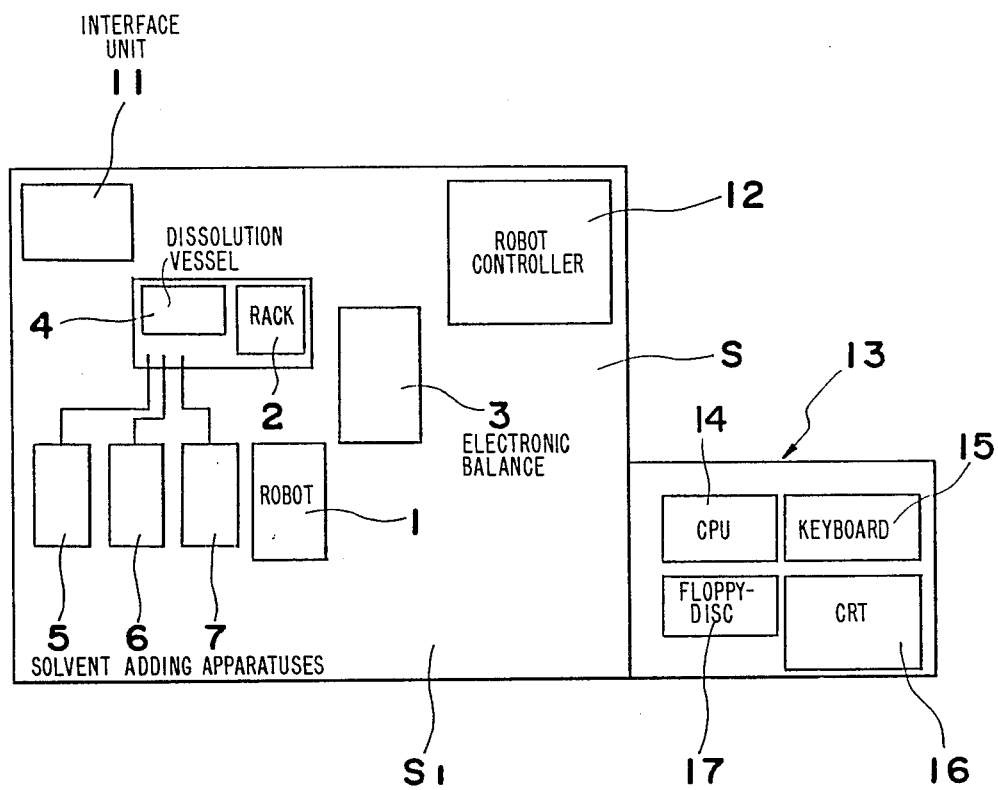
FIG. 1 is a schematic plan view of an automatic weighing and dissolution apparatus.

Before the description of the present invention proceeds, it is noted that like parts of the invention are designated by like reference numerals throughout the accompanying drawings.

Figure 2:
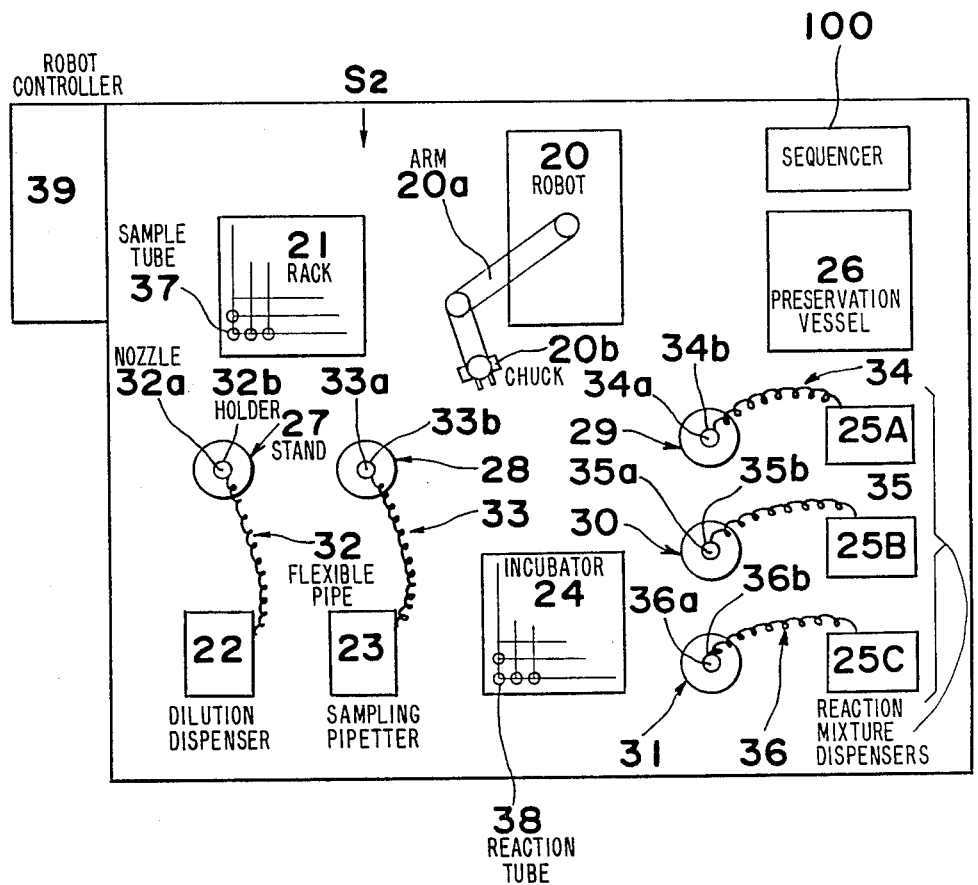
FIG. 2 is a schematic plan view of an automatic dilution and reacting apparatus.

The present automatic analysis apparatus is composed of an automatic weighing and dissolution apparatus shown in FIG. 1, an automatic dilution and reacting apparatus shown in FIG. 2, a FCI shown in and a data processing apparatus (not shown).

First, the construction and operation of the automatic weighing and dissolution apparatus shown in FIG. 1 will be described.

The present automatic weighing and dissolution apparatus is adapted to sequentially perform by the use of a robot, a computer, an electronic balance or the like, the operations of the pretreatment step such as the weighing of samples deposited into many sample tubes, the adding of a given amount of solvent to the sample corresponding to the weighing value, and the placing of the samples into a dissolution vessel for dissolving the samples into the solvent.

Figure 4A:
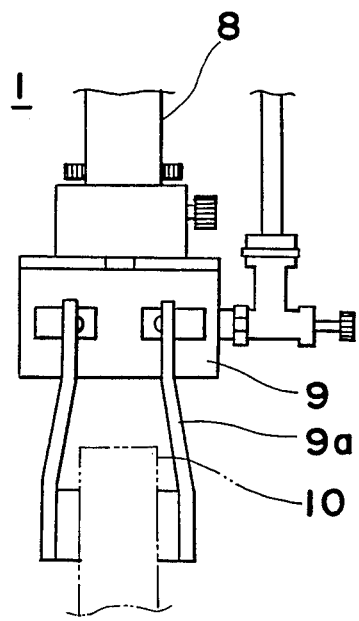
FIG. 4 shows, on an enlarged scale, a chuck of a robot, (A) being a front view, (B) being a plan view thereof.
Figure 4B:
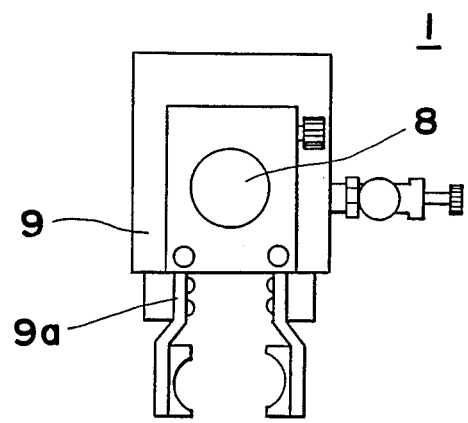

As shown in FIG. 1 and FIG. 4, a first automatic robot 1 is disposed in the approximate central portion of a work station S1, which has a rack 2 for retaining sample tubes, an electronic balance 3, a dissolution vessel 4 with a ultrasonicator attached thereto, and solvent adding appartuses (constant-amount dispensers) 5, 6, 7, all being disposed in different positions within the operation range of the robot 1. A sample tube 10 is held with a chuck 9, which is disposed on the tip end of an arm 8 of the robot 1 so that it may be carried to each of the apparatuses. It is noted that the dissolution vessel 4 is constructed as a dissolver, an extractor of mixer type or vibration type and the like.

Also, the work station S1 has an interface unit 11, a robot controller 12, and a factory computer 13 disposed beyond the operation range of the robot 1. The computer 13 is composed of a CPU (central processing unit) 14, a keyboard 15, a CRT (display apparatus) 16 and a floppy-disc (memory apparatus) 17.

Although a robot of a cylindrical coordinate, a polar coordinate, a rectangular coordinate or a multi-joint type, etc. are used as the robot 1, the multi-joint robot of a horizontal type is used in the present embodiment.

The robot 1 is 305 mm+295 mm in arm length, 220° for one shaft in the operation range, 300° for two shafts, 150 mm for Z, 360° for W in operation range, and 3200 mm per second in maximum composite speed. The present robot 1 has advantages in that the speed is faster, action range is wider, accuracy is better, and the operation is easier to assemble for multiple objects. The robot 1 is operated by the robot controller 12 to move the arm 8 into a given position and to open and close the chuck 9. As shown in FIG. 4, the chuck 9 detachably grasps the upper side portion of the sample tube 10 by a finger 9a mounted on the chuck 9 to carry the sample tube 10. It is noted that the finger 9a is made of polyurethane so that an impact may not be applied upon the sample tube 10 when the sample tube 10 has been grasped.

The specification of the robot controller 12 for operating the robot 1 adopts the maximum simultaneous four shafts in the number of the control shafts, a PTP system in the route control system, and a semi-closed loop system by the rotary encoder in the control system. The number of position settings is 500 in total of 30 steps×15, 50 steps×1, and the speed is variable in nine stages with 10 in input, 10 in output (0.1 through 60.00 seconds) in timer 8, 10 in memory.

Figure 5A:
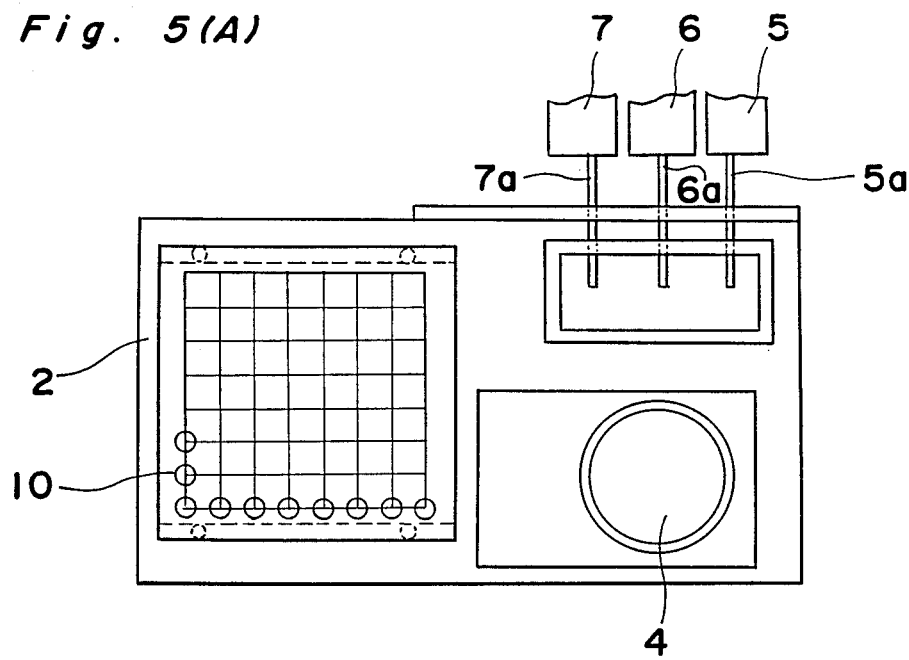
FIG. 5 shows a rack and nozzles of FIG. 1, and a dissolution vessel, (A) being a plan view, (B) being a front view thereof.
Figure 5B:
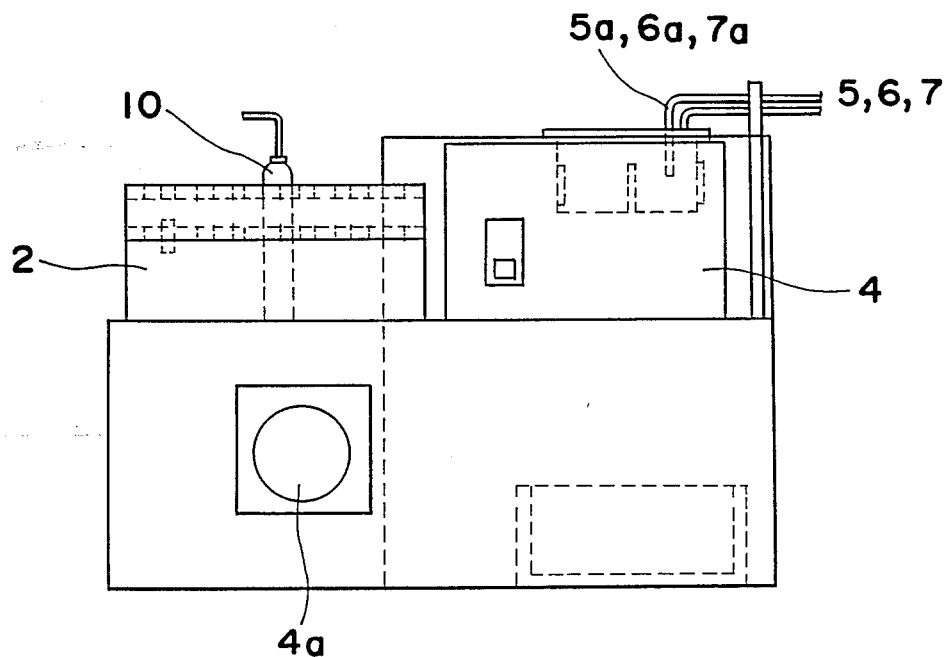

As shown in FIG. 5, the rack 2 has a sample tube 10 inserted into a hole for retaining the sample tube in an upright position; many sample tubes 10 are retained in longitudinal/lateral paralle. For easier insertion of the sample into the tube 10, the sample tube is adapted to be removed from the work station S1 with one grasp.

Figure 6A:
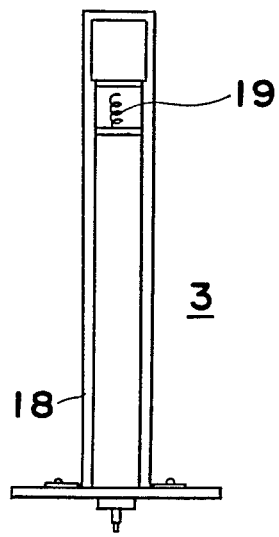
FIG. 6 shows a sample holder of an electronic balance, (A) being a front view, (B) being a side view, (C) being a plan view thereof.
Figure 6B:
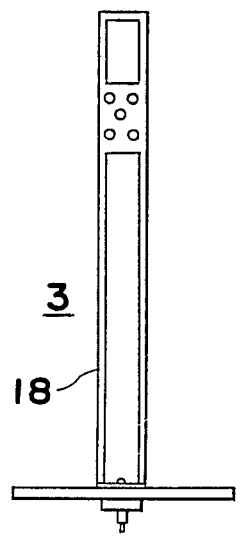
Figure 6C:
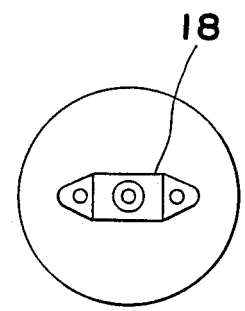

The electronic balance 3, which has a 30 g weighing limit and a 0.01 mg weighing accuracy, is capable of weighing 1 through 3 mg. A sample holder 18, shown in FIG. 6, on the balance 3 is made of aluminum as light as possible and is set to a weight of 22 g or less. The robot 1 is adapted to perform smoothly so that the robot 1 may put in and take out the sample tube 10 from above the electronic balance 3. The door of the electronic balance is adapted to open or close by a two-way cylinder (not shown) to be actuated through an electromagnetic valve which is connected with the robot so as to be controlled together by a controller of the robot. Also, when the robot 1 places the sample tube 10 on the upper portion of the holder 18, a spring 19 mounted on a sample receiver of the holder reduces the shock with respect to the balance so that the balance may be safely used. Also, the door of the electronic balance 3 is adapted to be closed and opened by the finger 9a of the chuck 9 of the robot 1.

A heater with a temperature controller 4a is mounted in the dissolution vessel 4 with the ultrasonicator. The heater is turned on, off, and in controlled by the computer 13 to maintain the temperature in the vessel at a desired constant temperature, usually 37° C. Also, when the sample tube 10 is placed by the robot 1 into the dissolution vessel 4, the ultrasonicator turns on. When the sample tube 10 is taken out, it is adapted to stop. The ultrasonicator is continuously used to prevent the temperature in the vessel from being increased.

As shown in FIG. 5, the solvent adding apparatuses 5, 6, and 7 are adapted to add solvent of different kinds to the sample tube 10 respectively from the nozzles 5a, 6a, and 7a. A digital diluter/pipetter is used as the solvent adding apparatus. A plurality of solvents are used, because not all samples are dissolved only in one type of solvent. In the present embodiment, water is added by apparatus 5, ethanol by apparatus 6, and dimethyl formamide by apparatus 7.

The amount of solvent added by the solvent adding apparatuses 5 through 7 is set through a calculation from the molecular weight and the concentration which are inputted in advance in the computer 13 in accordance with the weight of the sample weighed by the electronic balance 3, so that a set amount is added into the sample tube from the nozzle.

At the completion of the solvent addition, the sample tube 10 is moved a little by the robot 1 to cause the solvent liquid at the nozzle tip end to come into contact against the inner wall of the sample tube 10 so that the given amount of solvent may be completely injected into the sample tube 10.

Figure 7:
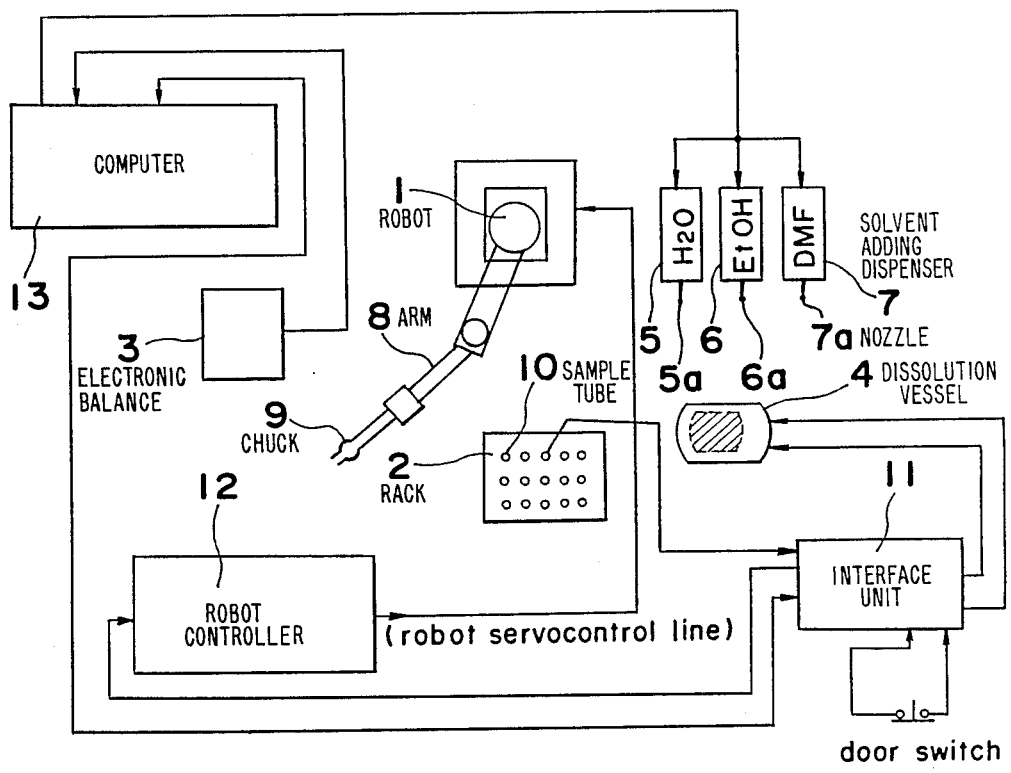
FIG. 7 is a control circuit diagram of the apparatus of FIG. 1.
Figure 8:
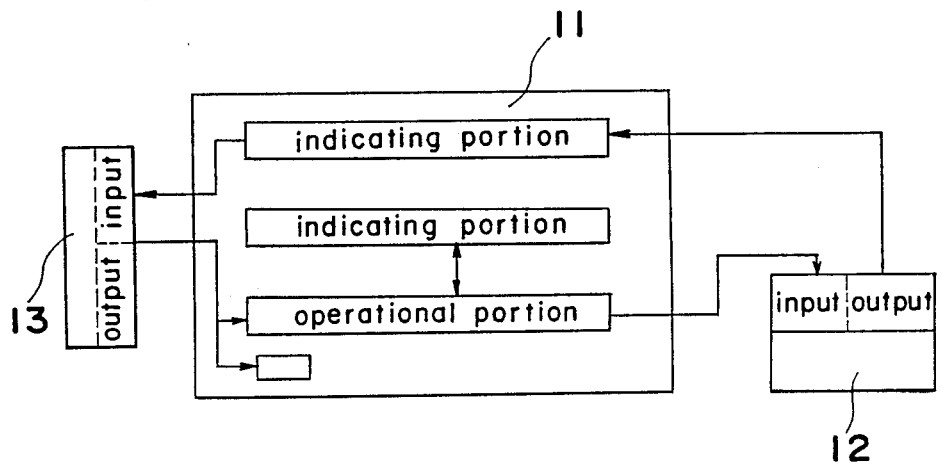
FIG. 8 is a schematic diagram of an interface unit.

The entire controlling line of this apparatus is shown in schematic FIG. 7. The schematic construction of the interface unit 11 is schematically shown in FIG. 8. The program input into the computer 13 is shown in the block diagram of FIG. 9. The sample information, with respect to the total number of samples, the number of the sample, the molecular weight, the dissolution concentration and the solvent name input into the computer 13 in advance of the start of the program, so that the desired dissolution may be performed.

Figure 10B:
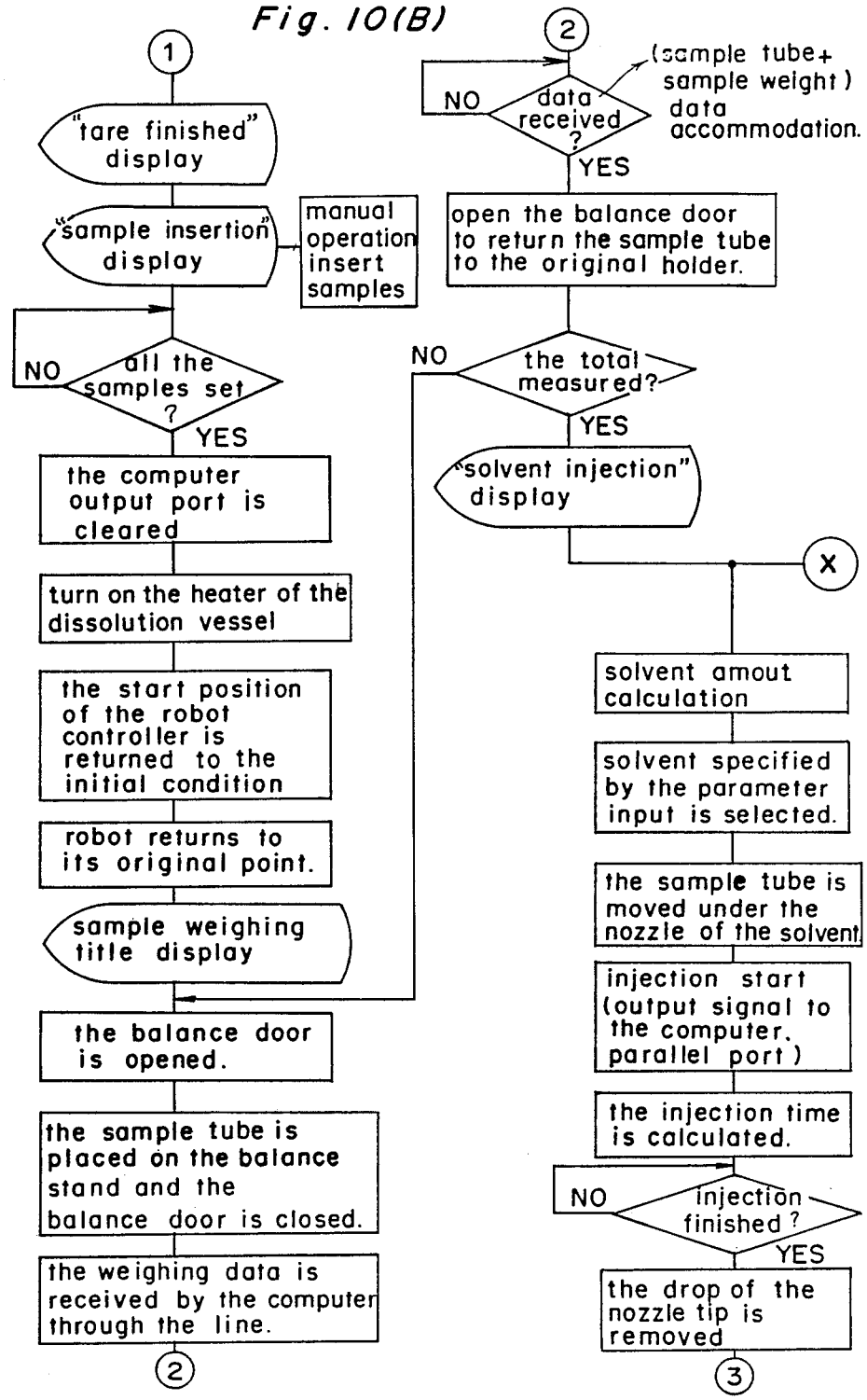
Figure 10C:
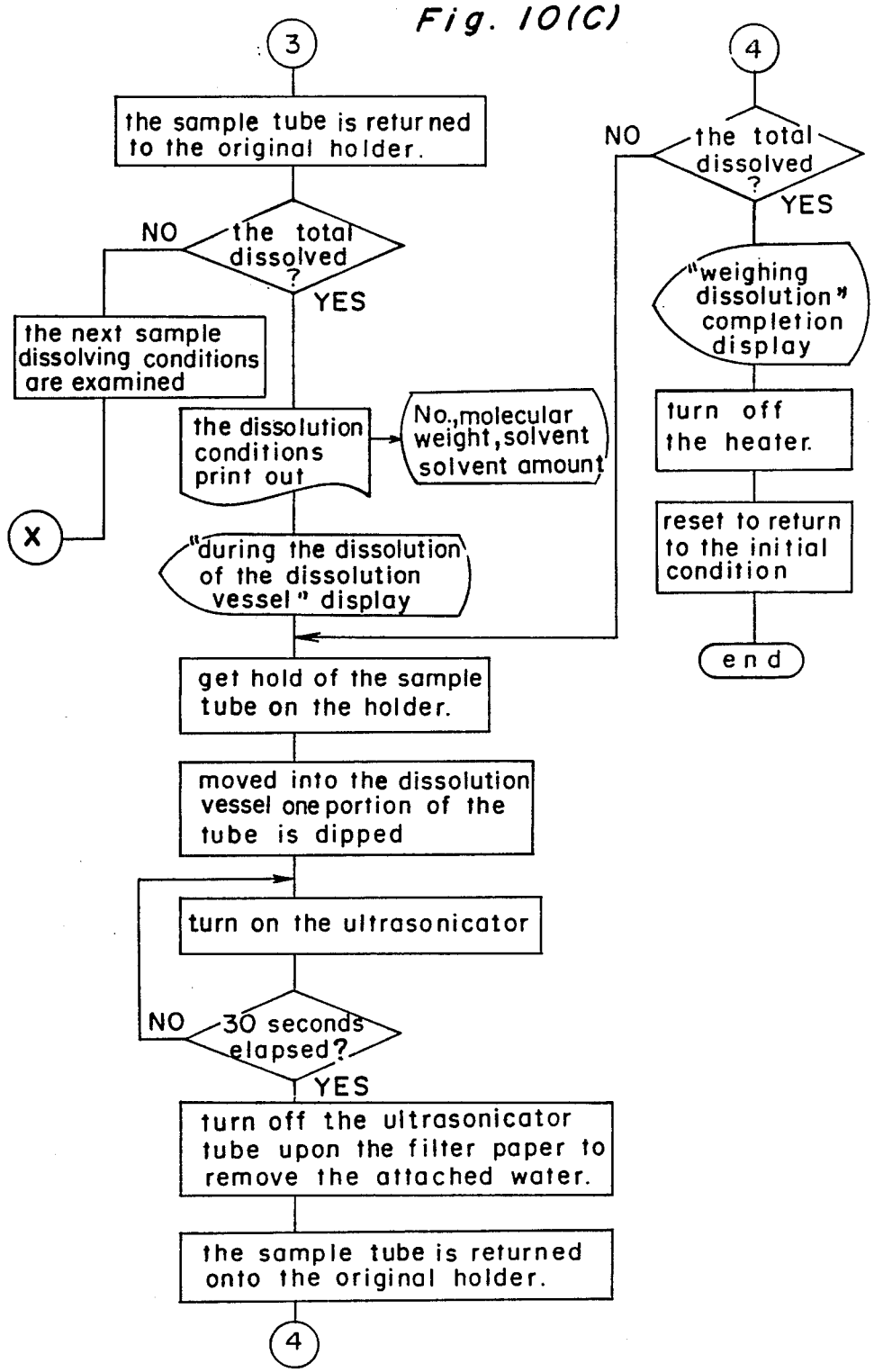

The weighing operation and the dissolving operation performed by the apparatus is made in the order described hereinafter. As the operation is effected in such an order as shown in FIG. 10, the arm 8 of the robot 1 is restored to the original point before the start of the program and the empty tubes 10 are arranged in the rack 2.

(1) The sample information is input into the computer 13.

Namely, the total number of the samples, the lot number, the molecular weight, the dissolution concentration, and the solvent to be added are input.

(2) The weighing of the empty sample tube 10 is effected.

Namely, the door of the electronic balance 3 is opened with the chuck 9 of the robot 1 (it is noted that all of the following operations are performed by the finger 9a of the chuck 9 of the robot 1). → The sample tube 10 is moved from the rack 2 into the balance 3 and on the holder 18. → The door is closed. The sample tube 10 is weighed (tare weighing). → The door is opened. → The sample tube 10 is moved into the rack 2 from the balance 3. → The above-described operation is repeated for all the sample tubes 10.

(3) Then, a sample of 1 to 3 mg is manually added to each of the sample tubes.

(4) Then, the sample weighing operation is effected.

As in the previous weighing operation, the sample tube 10 is moved into the electronic balance 3 from the rack 2 with the chuck 9 of the robot 1 for the weighing operation. It is restored into the rack 2 after the weighing operation. The operation is repeated for all the sample tubes.

The weighing data obtained from the balance 3 is input into the computer 13. The kind of solvent to be added, and the amount of the addition are set through the calculation from the molecular weight and the concentration which are input in advance into the computer 13.

(5) Then, the solvent addition is performed.

Namely, the sample tube 10 is grasped from the rack 2 by the finger 9a of the chuck 9 of the robot 1 and moved to the nozzle tip end of the specified solvent adding apparatuses 5, 6, or 7 to add the solvent of the set amount for the calculated time. After the injection, the arm 8 of the robot 1 is moved a little to cause the solvent at the nozzle tip end to come into contact against the inner wall of the sample tube 10 to completely add the set amount.

When a solvent of two or three kinds is required, the sample tube is moved to the other solvent adding apparatus after the addition of solvent by one adding apparatus and that solvent is added. The sample tube is returned to the rack 2 after the solvent addition. The operation is repeated for all the sample tubes.

(6) Then, the dissolution of the sample is effected.

Namely, the sample tube 10 in the rack 2 is moved into the dissolution vessel 4 with an ultrasonicator by the robot 1 and a portion of the sample tube 10 is dipped into the vessel. The sample tube is kept for thirty seconds within the dissolution vessel 4 and the sample is dissolved in the solvent. The dissolution vessel 4 is normally maintained at 37° C. When the sample tube 10 is placed into vessel 4, the ultrasonicator turns on. When the sample tube is taken out, the ultrasonicator is turned off. The sample tube 10 which has been taken out of the dissolution vessel 4 is touched against filter paper to remove the attached water and then returned to its original place in the rack 2 by the robot 1. This operation is performed on all the sample tubes 10 to dissolve all the samples.

As shown in the ⊓-shaped blocks of FIG. 10, each operation is displayed by the CRT 16. Also, the test results of the sample tube 10 as shown hereinabove are printed out on a piece of paper by a printer (not shown) so that the test results may be easily confirmed.

The enzyme dilution and reacting apparatus shown in FIG. 2 has disposed in different positions around a second automatic robot a rack for retaining a plurality of sample tubes, a dilution dispenser, a sampling pipetter, an incubator with a plurality of reaction tubes disposed therein and reaction mixture dispensers. The nozzles are mounted respectively through flexible pipes in each dispenser. These nozzles are detachably retained in nozzle stands disposed in the operation range of the robot. Each of the nozzles is freely grasped with the chuck provided on the arm of the robot so that it is moved into the opening of the sample tube in the rack or of the dilution reaction tube in the incubator. The robot is operated by the controller to inject the diluted solution into the sample tube in the rack from the dilution dispenser. The diluted sample is sampled from the sample tube by the sampling pipetter and injected into the reaction tube within the incubator. The reaction mixture which is an enzyme solution such as cells, arachidonic acid, ethanol, etc. is sequentially added from the reaction mixture dispensers into given diluted sample in the incubator after given periods of time so as to effect the reacting operation.

As shown in FIG. 2, an automatic robot 20 is disposed in a central position on a rear side of the work station S2, while a rack 21 for diluting the original solution, a dilution dispenser 22, a sampling pipetter 23, an incubator 24, reaction mixture dispensers 25A, 25B, 25C and a preservation vessel 26 are disposed in a counter clockwise fashion at different positions on the periphery of the work station within the operation range of the robot 20. Also, nozzle stands 27, 28, 29, 30, and 31 are set respectively on the side of each of the dispensers 22, 23, 25A, 25B, and 25C to detachably retain nozzles 32a through 36a which are integrally formed on the tip ends of the flexible pipes connected with the respective dispensers 22 through 25C. The nozzle holders 32b through 36b are engaged with these nozzles 32a through 36a. The nozzle holders 32b through 36b are grasped with a chuck 20b disposed on the tip end of an arm 20a of the robot 20 so that they are adapted to be moved into the opening portion of a sample tube 37 in the rack 21 or of a reaction tube 38 in the incubator 24. Also, a robot controller 39 is disposed beyond the operation range of the robot 20 on the work station S2 to automatically control the robot 20.

The cylindrical coordinate, polar coordinate, rectangular coordinate and multi-joint, etc. type robot can be used in this apparatus as in the automatic weighing and dissolution apparatus, but in the present embodiment, the horizontal multi-joint type robot 20 is used. The robot 20 is cylindrical in the work range of 800 mm in radius, 300 mm in height. The first articulation and the second articulation (X,Y axes), the third articulation (Z axis), and the fourth articulation ($\theta$ axis) may be simultaneously controlled. The portable weight is 10 kg with 75/100 in speed, and the reproducibility of the position is $\pm 0.05$ mm.

The present robot 20 has advantages in that the speed is faster, the operation range is wider, the precision is better, and the operations are likely to be built-up for multiple objects. The robot 20 is operated by the robot controller 39 to move the arm 20a to a given position so as to perform the opening and closing operations of the chuck 20b. The chuck 20b detachably grasps the nozzle holders 32b through 36b by the finger mounted on the chuck 20b as in the robot 1 or freely grabs the reaction tube 38 to carry it. Also, the object grasped and carried with the chuck 20b with the finger being 24 mm in full opening is restricted in width to 12 mm in diameter, and the sample tube 37, the reaction tube 38, and the nozzle holders 32b through 36b are the same in diameter. It is noted that the finger is similar to 9a of FIG. 4.

Figure 11A:
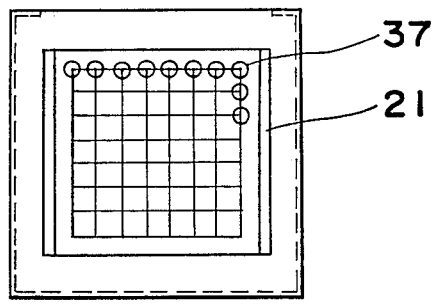
FIG. 11 shows, on an enlarged scale, a rack 21 of FIG. 2, (A) being a plan view, (B) being a front view thereof.
Figure 11B:
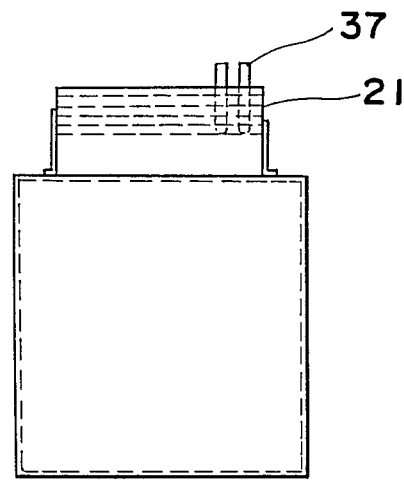

The rack 21 for diluting the original solution is of such construction as shown in FIG. 11. The rack has holes of 12 mm in diameter arranged at a distance of 25 mm in eight columns, eight lines in accordance with the instructions of the robot 20. The racks in the incubator 24 and the preservation vessel 26 are similar in constructiion. Some sample tubes 37 retained by the rack 21 have the sample solution deposited thereinto, other sample tubes are empty.

The dilution dispense 22 uses a digital diluter/pipetter, having original point detection, self-flushing, self-examination, and air layer constituting functions using a two-syringe system through the controlling operation of the 8-bit microprocessor. Its capacity range is 5 through 250 µl on the test side, 0.05 through 9.99 ml on the sample side. When the precision is $\pm 1\%$ of the syringe maximum capacity, the operation speed is three seconds, in half cycle with syringe of 1 ml and also five seconds with syringe of 2.5 ml.

The flexible pipe 32 for feeding the diluted solution into the sample tube 37 from the dispenser 22 is Teflon tube (2 m in length, 1 mm in inner diameter) made into a coil-shape 10 mm in diameter. The nozzle 32a is formed at the tip end of the tube to integrate the flexible pipe with the nozzle. The cylindrical Teflon-made nozzle holder 32b of 12 mm in diameter, 70 mm in height is fixedly engaged with the nozzle 32a in the location of 100 mm from the tip end to prevent flexibility in the expansion and to retain injection precision. The sampling pipetter 23, the reaction mixture dispensers 25A, 25B, 25C, the flexible pipes 32 through 36 coupled to them, the nozzles 32a through 36a, and the respective nozzle holders 32b through 36b are the same in constructiion as the dilution dispenser 22.

Figure 12A:
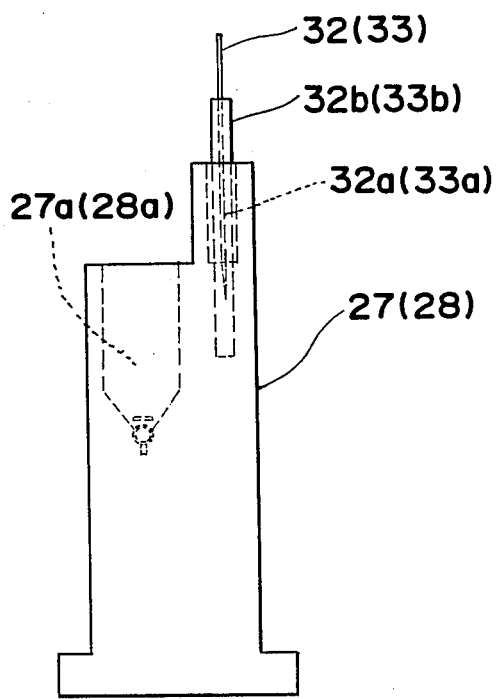
FIG. 12(A) is a front view of a nozzle stand of a dilution dispenser and a sampling pipetter.

Flushing vessels 27a, 28a for flushing the nozzles 32a, 33a are provided as shown in FIG. 12(A) on the nozzle stands 27, 28 for detachably retaining the nozzles 32a, 33a of the dilution dispenser 22 and the sampling pipetter 23, so that the tip end of the nozzle for each completion of the sampling is dipped to flush the exterior side. The flushing operation of the nozzle interior is performed simultaneously with the injection of the diluted solution, so that the flushing operation is not required to be effected for each sample.

Figure 12B:
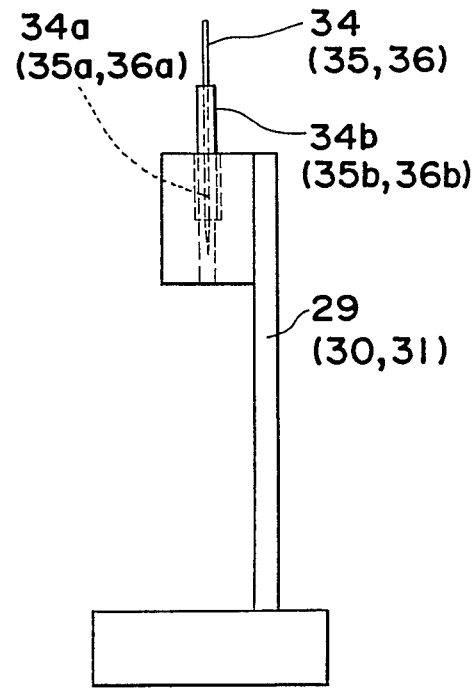
FIG. 12(B) is a front view of a nozzle stand of a reaction mixture dispenser.

On the other hand, the nozzles 34a through 36a of the reaction mixture dispensers 25A, 25B, 25C are not required to be flushed, so that the flushing vessels are not disposed as shown in FIG. 12(B) on the nozzle stands 29, 30, 31.

Figure 13A:
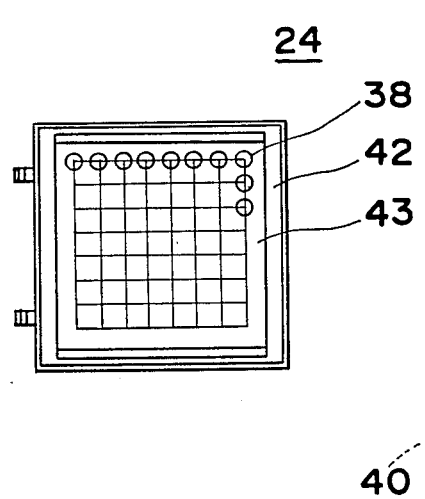
FIG. 13 shows, on an enlarged scale, an incubator, (A) being a plan view, (B) being a front view thereof.
Figure 13B:
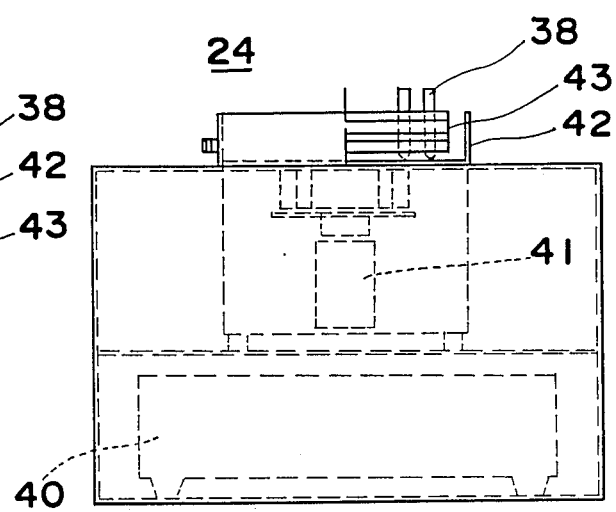

The incubator 24 is of such construction as shown in FIG. 13(A), (B) and has a circulating jet type thermostat 40 at the lower stage. The apparatus 40 circulates thermostatic water of the jet type and has an accuracy of controlling the temperture of 0.1° C. using a thermistor ON/OFF system between the room temperature +5° C. through 60° C. (heater 400 W). Also, a magnetic stirred 41 is provided at the middle stage of the incubator 24, and a thermostat 42 is disposed at the upper stage to retain the interior of the thermostat 42 at 37° C. in the embodiment. A rack 43 similar to the rack 21 is disposed in the thermostat 42. Also, a blister-sterol made liquid-level detector (not shown) of a floating type is mounted in the thermostat 42. When the liquid in the vessel reduces, the blister-sterol lowers to operate an alarm by a microswitch mounted under it to stop the robot 20. The reaction tube 38 retained in the rack 43 of the incubator 24 is the same in diameter, i.e., 12 mm as the sample tube 37. A magnetic stirrer bar of 5 mm in diameter is placed in advance in the reaction tube 38 so that the stirring of hand-drum shape is caused by the magnetic stirrer 41, which is provided with a magnet of 20 cm in diameter. The stirring of 64 reaction tubes 38 can be simultaneously effected by one stirrer. Also, a temperature control apparatus which may be set at a desired temperature is mounted as the heater is used in the present incubator, and in the present embodiment, the temperature is retained at 37° C.

Figure 14A:
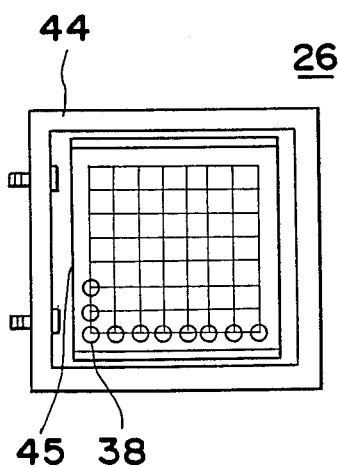
FIG. 14 shows, on an enlarged scale, a preservation vessel, (A) being a plan view, (B) being a front view thereof.
Figure 14B:
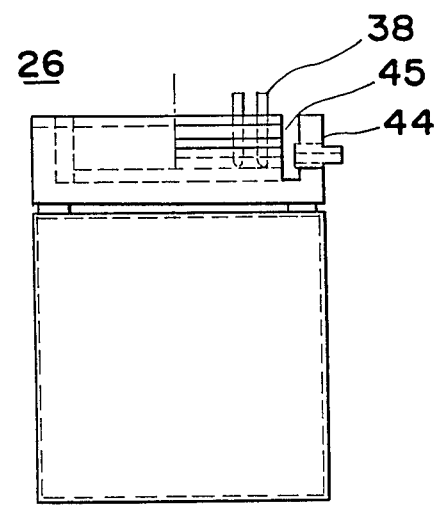

The preservation vessel 26 is of such construction as shown in FIG. 14(A), (B). Water is circulated by a cool-water circulating machine. The cooling system is a liquid expansion type having an adjustable temperature range of 0° C. through room temperature and about 120 Kcal per hour in cooling performance. Also a temperature control apparatus which may be set at a desired temperature is mounted as a safety apparatus. The temperature is 0° C. in the present embodiment. The cooling water retained at the set temperature is circulated into the cooling vessel to retain the temperature at the optional temperature with a rack 45 similar to the rack 21 being disposed in the preservation vessel 26. Also, a floating type of liquid-level detector (not shown) is mounted in a thermostat 44 so that the blistersterol lowers as the liquid in the vessel reduces. A microswitch mounted under it actuates an alarm to stop the robot 20.

Figure 3A:
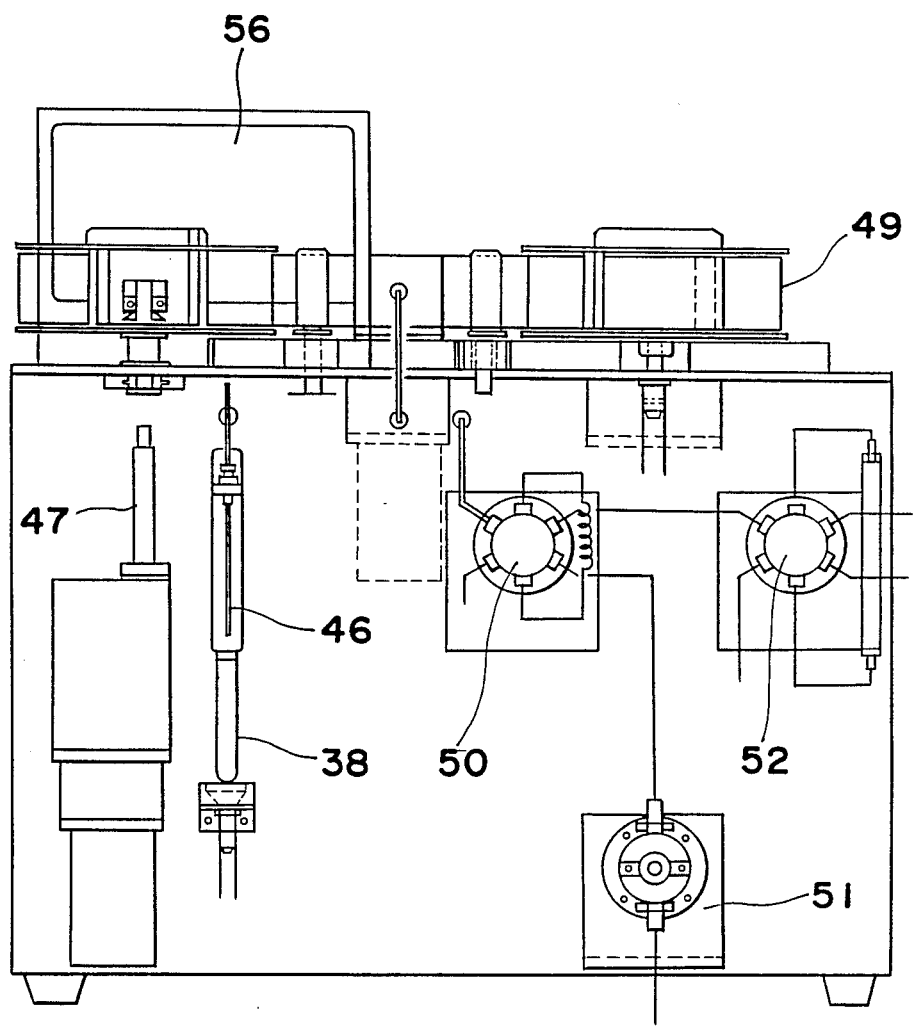
FIG. 3 shows an automatic filtration, concentration, and injection apparatus, (A) being a front view, (B) being a plan view thereof.
Figure 3B:
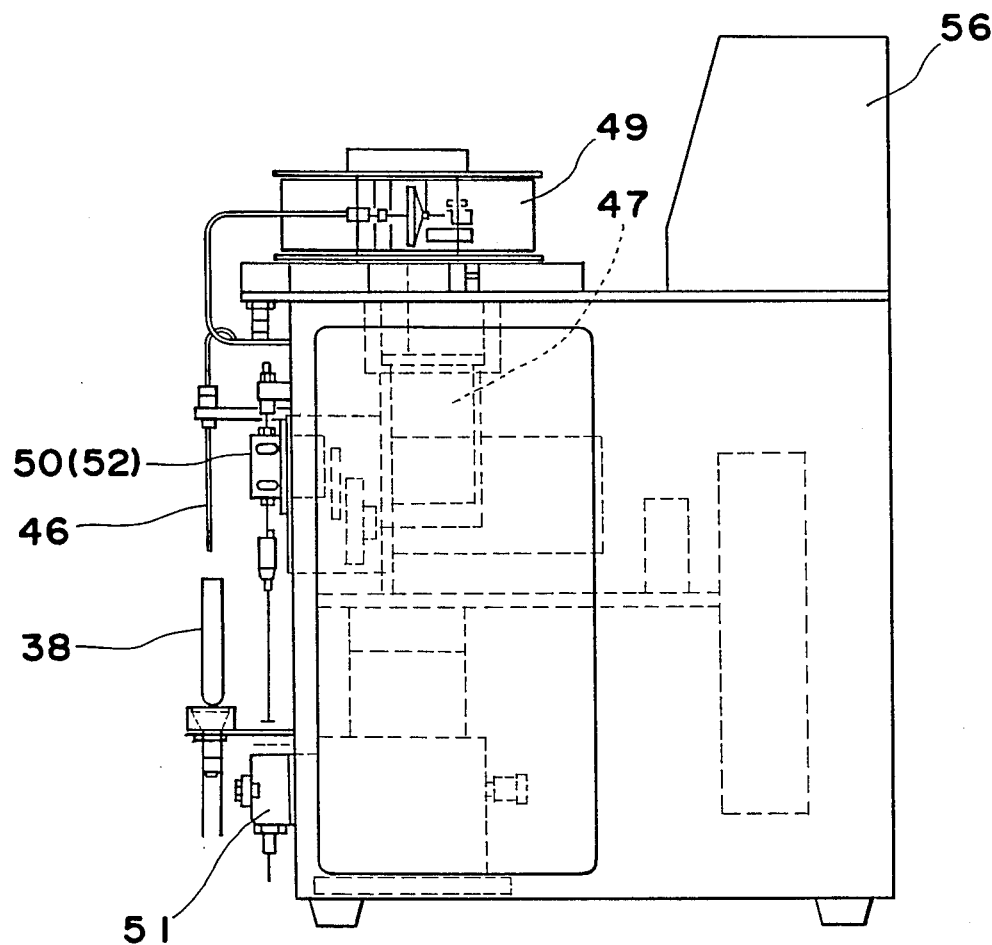

The FCI performs filtration and concentration of the reaction mixture, shown in FIG. 3, and performs the on-line injection into the HPLC. It is disposed adjacent to the work station S1 of the automatic dilution and reacting apparatus, so that the reaction tube 38 which is preserved by the preservation vessel 26 is adapted to be moved onto the FCI by the robot 20.

Figure 15:
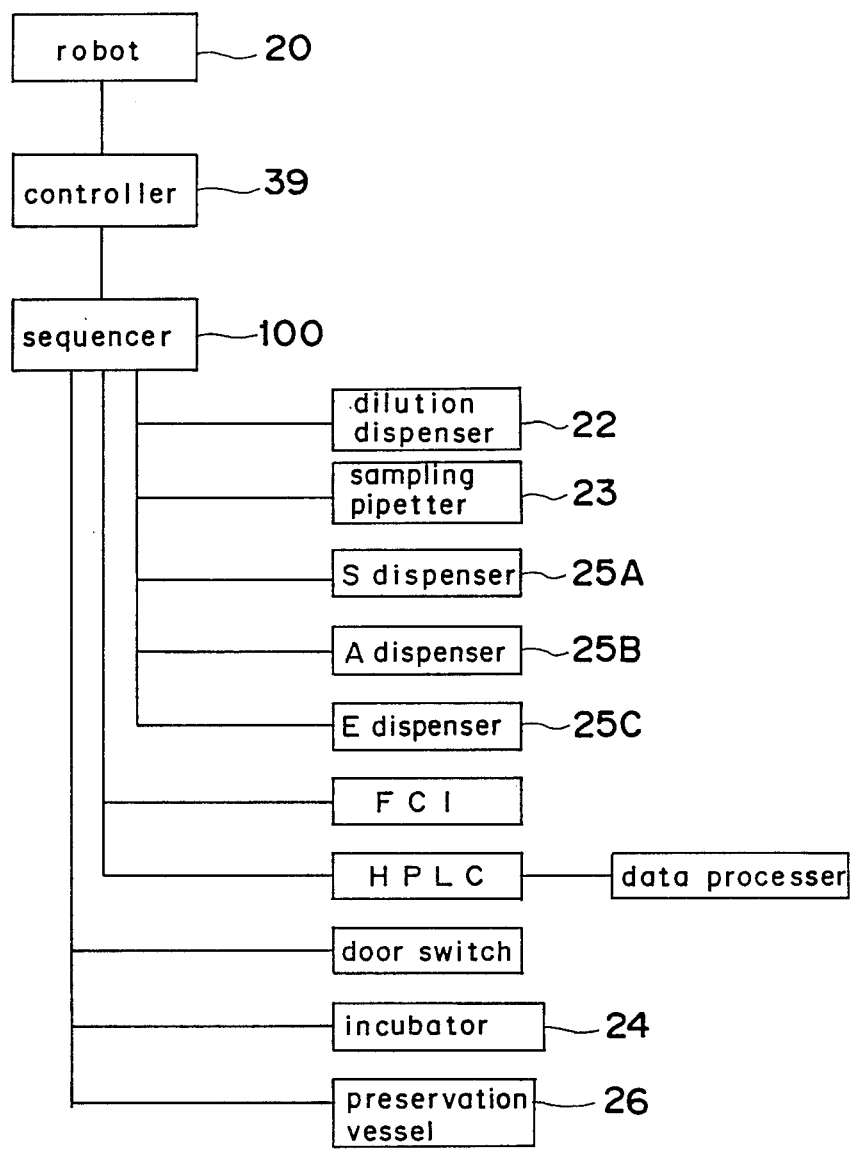
FIG. 15 is a schematic diagram of the system of an automatic dilution and reacting apparatus.
Figure 16:
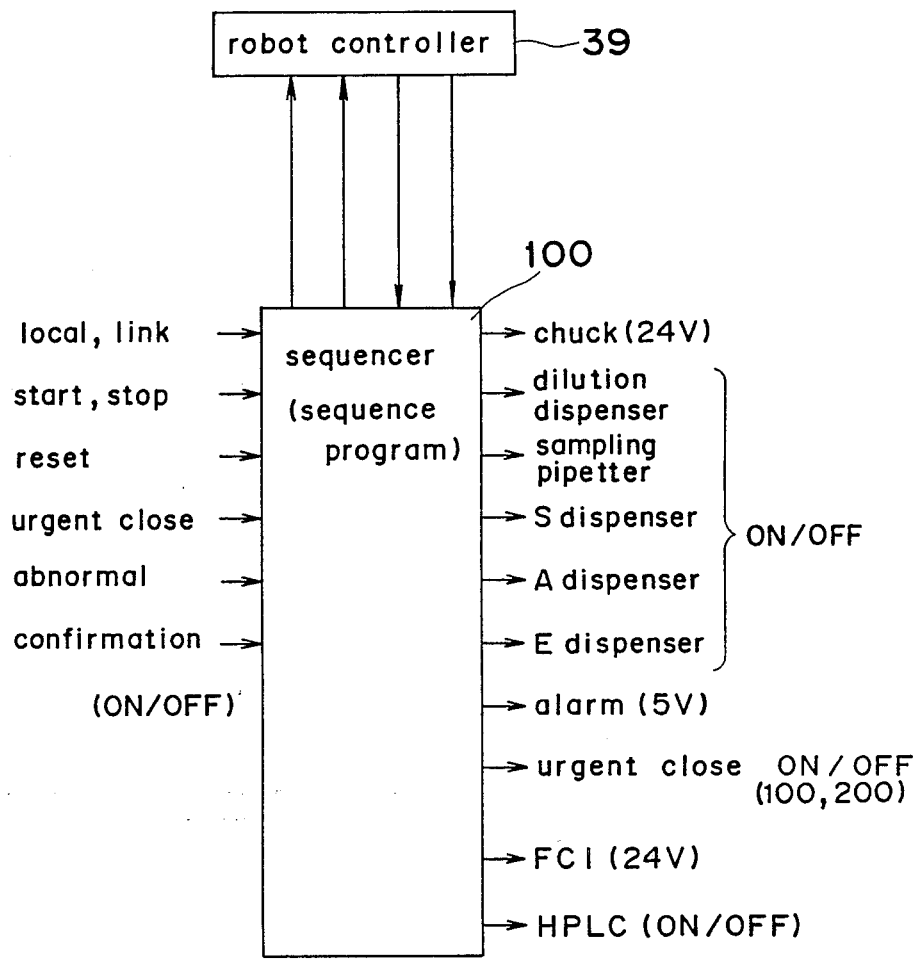
FIG. 16 is an electronic schematic diagram showing electric connections.
Figure 17:
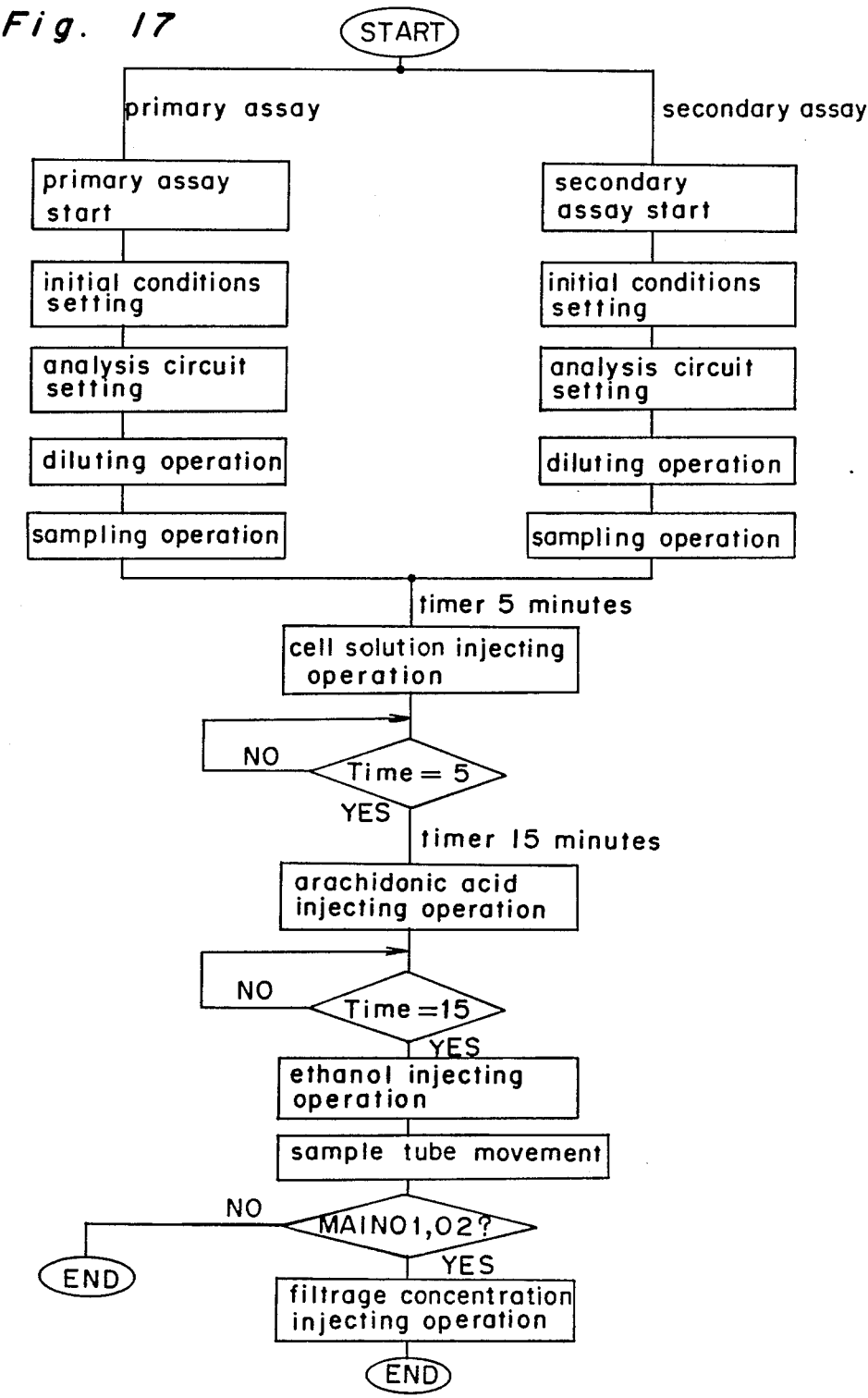
FIG. 17 is a flow chart showing the operation sequence.

The construction of the system of the automatic dilution and reacting apparatus of the present invention is shown in FIG. 15. The robot 20 has the robot controller 39 connected with a sequencer 100. The dispensers 22, 23, 25A, 25B, 25C, the incubator 24, the preservation vessel 26 and the FCI, the HPLC, the door switch of the electronic balance, the temperature control apparatus, and the liquid-level detector are also connected with the sequencer 100, which electric connections are shown in FIG. 16. The operation of the present dilution and reacting apparatus is shown in the flow chart of FIG. 17. The analytical method provides for two types of assays, the primary assay of the rough investigation and the secondary assay of the minute investigation.

The operation of the present apparatus will be described hereinafter using lipoxygenase as the enzyme.

RBL-1 is used as the source of lipoxygenase. The cells are cultured in BPM-1640 culture solution containing 10% bovine embryo blood serum, washed, and thereafter suspended in the saline. The RBL-1 is prepared as $1 \times 10^7$ cell per ml. The cell suspension is added from the reaction mixture dispenser 25A, arachidonic acid is added from the dispenser 25B, and ethanol from the dispenser 25C. Also, dimethyl formamide is injected from the dilution dispenser 22.

At the operation start for the following processes, the arm 20a of the robot 20 is restored to the original point by the robot controller 39. Thereafter, the operation of the robot 20 is effected by the robot controller 39. Also, respective dispensers 22 through 25C operate so that the reagent which is filled in each respective reagent bottle in advance is full in the cylinder and the flexible pipe.

(1) First, the diluting operation of the sample is performed. Namely, the nozzle holder 32b of the nozzle 32 of the dilution dispenser 22 is grasped with the chuck 20a of the robot 20 to move the nozzle 32 for taking a sampling by the dilution dispenser 22 of a given amount of dissolved sample solution 37A located in the rack 21 shown in FIG. 11 and FIG. 18 to inject the dilution solution from the dilution dispenser 22 into the empty sample tube 37B. In the drawings, reference numeral 37C is a sample tube for control use.

Figure 18A:
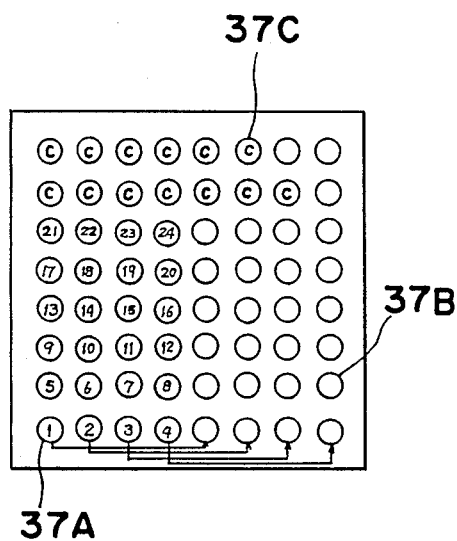
FIGS. 18(A) and (B) show the arrangement of sample tubes on the rack 21.
Figure 18B:
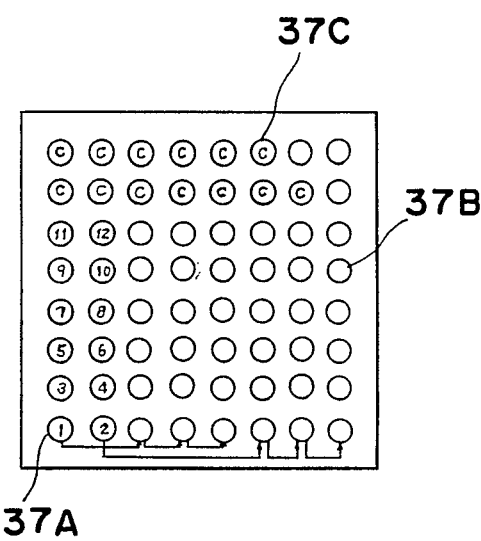

In the diluting operation, the primary assay, or the secondary assay is selected, and the number of the samples are input so that the robot 20 is operated as described hereinabove. 63 sample tubes 37 at a maximum are arranged on the rack 21, the number of the samples per cycle is 24 in the primary assay shown in FIG. 18(A), 12 in the second assay shown in FIG. 18(B) for the analysis of the control at the rate of one of four. In the diluting operation, the multiple diluting method is adopted of 10 times in primary assay, and 10 times, 100 times, 1,000 times in the secondary assay. The dispenser 22 is set with syringe 100 μl, suction amount 100 μl on the sample side, Vol. mode, syringe 1 ml, suction amount 0.9 ml on the reagent side.

(2) The sampling operation is performed after the dilution. Namely, the holder 33b of the nozzle 33a of the sampling pipetter 23 is grasped with the chuck 20b of the robot 20 for taking a sampling of the diluted sample at 10 μl respectively from the sample tube 37 after the dilution in the rack 21 to inject it into the empty reaction tube 38 arranged in the rack in the incubator 24. During the process, the sampling pipetter 23 is set with syringe 50 μl, suction amount 10 μl, on the sample side, Vol mode, syringe 1 ml, suction amount 0.1 ml on the reagent side. In this method, the washing operation of the flexible pipe is completely performed as the reagent is discharged after the discharging of the sample. The external side of the flexible pipe is washed with the tip end of the flexible pipe being dipped after each sampling in the washing vessel 28a disposed on the nozzle stand 28.

The diluted sample in the reaction tube 38 is stirred through the rotor disposed in advance in the reaction tube 38 by the magnetic stirrer 41 after the injection.

(3) Then, addition of the cell suspension is performed. Namely, the holder 34b of the nozzle 34a of the dispenser 25A is grasped with the chuck 20b of the robot 20 to move it to each reaction tube 38 in the incubator 24 to add 1 ml of the prepared RBL-1 cell suspension into the reaction tube 38. Thus, the dispenser 25A is set with 0 on the sample side, Vol mode, syringe 2.5 ml, syringe capacity 1 ml, capacity 0.4 on the reagent side. Immediately before the cell suspension is injected, the timer of the controller is set to 5 minutes so that when the cell suspension is injected, a preincubation period is allowed for five minutes.

(4) Then, the addition of the arachidonic acid is performed. When the timer reaches zero (and the preincubation is completed), the timer is reset to 15 minutes for the reaction with the arachidonic acid. Namely, the holder 35b of the nozzle 35a of the dispenser 25B is grasped with the robot 20 to move it to the reaction tube 38 to inject the arachidonic acid 50 $\mu$g+calcium-ionofor A-23187 1 mg/100 $\mu$l. The dispenser 25B at this time is set, with 0 on the sample side, Vol mode, syringe 250 $\mu$l, syringe capacity 1 ml, capacity 0.4 on the reagent side, to inject 0.1 ml (0.25 ml×0.4).

(5) Then, the addition of the ethanol is performed.

When the timer reaches zero (and the reaction is completed) after 15 minutes, ethanol is injected by 1 ml to stop the reaction. Namely, the nozzle 36a of the dispenser 25C is grasped with the chuck 20b of the robot 20 to move it to the reaction tube 38 to inject 92% ethanol, at 1.2 ml, containing the GEDTA 1 mg. At this time, the dispenser 25C is set with 0 on the sample side, Vol. mode, syringe 2.5 ml, syringe capacity 1 ml, capacity 0.4 on the reagent.

(6) The reaction mixture preservation is performed after the reaction. Namely, the reaction tube 38 in the incubator 24 is grasped with the chuck 20b of the robot 20 to place it in the preservation vessel 26 to preserve the reaction mixture.

The operation described hereinabove analyzes the lipoxygenase reaction by the use of the RBL-1 cell. In order to analyze the cyclooxygenase reaction, rat platelets, instead of the RBL-1 cell, is used. Blood is drawn from the rat abdominal aorta with the use of 3.2% sodium citrate and centrifuged at room temperature. The rat platelets are prepared so that the concentration of the platelets become $1\times10^9$ cell per ml.

The analysis of the cyclooxygenase reaction is similar to that of the lipoxygenase reaction. The prepared platelets are added to the reaction tube 38 from the dispenser 25A. Namely, the platelets of 0.25 ml are added to the diluted sample 10 $\mu$l in the reaction tube 38. After five minutes preincubation, the arachidonic acid of 125 $\mu$g per 25 $\mu$l is added from the dispenser 25B to perform the reaction for fifteen minutes. Then, ethanol of 1.0 ml is injected from the dispenser 25C to stop the reaction.

Although any enzyme may be used in the present reaction, an enzyme showing biological reaction is preferable with the substrate and the product of the enzyme reaction being extremely small in amount. For example, the lipoxygenase or the cyclooxygenase enzymes are preferable with the products being leukotrienes, prostaglandins, thromboxanes. A refined enzyme preparation may of course be used. Such tissue cells themselves as described in the embodiment may be used.

The automatic filtration, concentration and injection apparatus shown in FIG. 3 uses a filtrating system for on-line use, instead of the conventional centrifugation system, to remove the admixture of protein or the like. A system for continuously winding the filter paper which is simpler and more inexpensive is used in the apparatus as the filtration system, i.e., a system of having a band-shaped filter paper is placed on the passage, taken up after the filtration and replaced with new paper. Also, in the concentration operation, the present system adopts a concentration method with a precolumn, because a reversed phase HPLC is used in the identification and estimation of the products. Namely, a preliminary column (concentration column) of a small size for absorbing the sample is disposed before the analysis column, and the sample is dissolved in solvent which is higher in polarity than the eluate. When it is moved through the column the object material is adsorbed. Then it is continuously guided into the analysis column from the concentration column with the eluate, so the concentration may be performed by the on-line system at the same time as the separation and estimation of the sample. When a sample of 1 ml is injected into the concentration column, a sensibility increase of 20 through 50 times is caused in the injection amount (20 through 50 $\mu$l) in the conventional HPLC. Also, the filtration apparatus is coupled to the concentration apparatus, to which an HPLC injection apparatus is mounted by a six-way valve switch, which apparatuses together become the FCI. Hence, the operations for filtration→concentration→injection into the HPLC may be automatically effected by the apparatus.

Specifically, the apparatus comprises a sampling nozzle 46 for sampling the reaction mixture from the reaction tube 38, a syringe pump 47 for sucking or discharging the solution drawn from the reaction tube 38 with the sampling nozzle 46 and the water in the tank 55, a capacity adjusting loop 48 for introduction of the sampling reaction mixture, a filtration unit 49 for filtering of the reaction mixture to be fed from the capacity adjusting loop 48 using a filter paper continuous winding type, a six-way valve 50 with a sampling loop to which the filtered reaction mixture is fed, a water pump 51 for feeding the reaction mixture in the loop of the six-way valve 50A with the water, a six-way valve 52 with a concentration column to which the reaction mixture is fed by the water pump 51, and an analytic pump of HPLC for feeding the eluate to the concentration column 52B to inject into the analytic column the sample solution in the concentration column.

The above-described sampling needle 46 has a vertical operation range of 10 cm to simplify the interlocking operation with the robot 20. The filtration unit 49 has a roll-shaped filter paper that is 50 m in length, 50 mm in width, 0.45 $\mu$m in the hole diameter so that it may be continuously used about 3,000 times. Also, the capacity adjusting loop 48 and the sampling loop 50B are externally disposed for easier variation in the solution amount.

Figure 20:
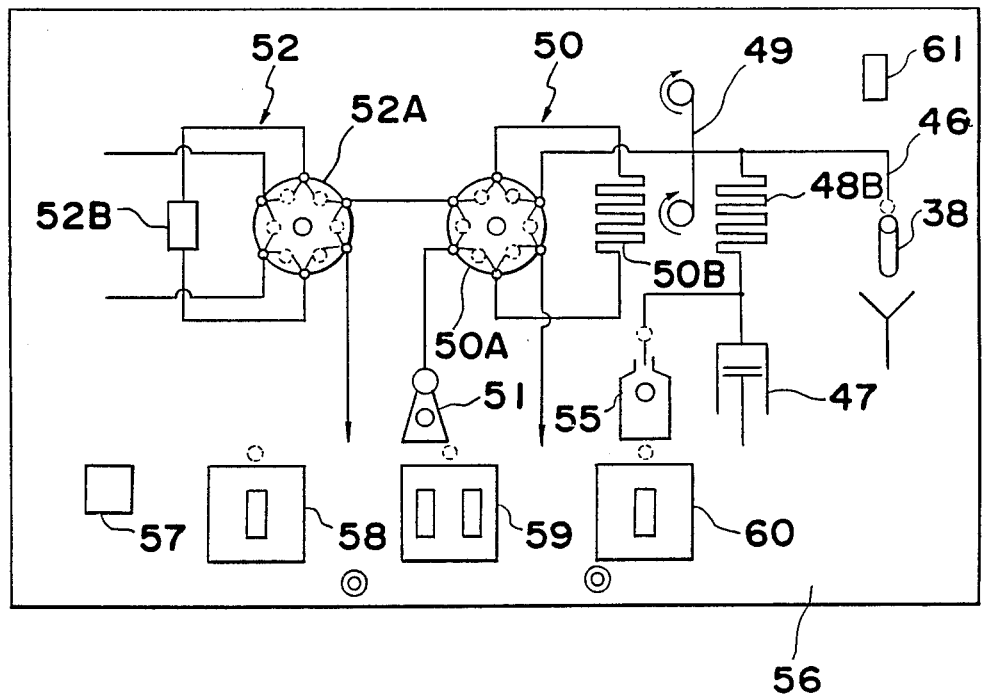
FIG. 20 is a front view of an operation panel.
Figure 19:
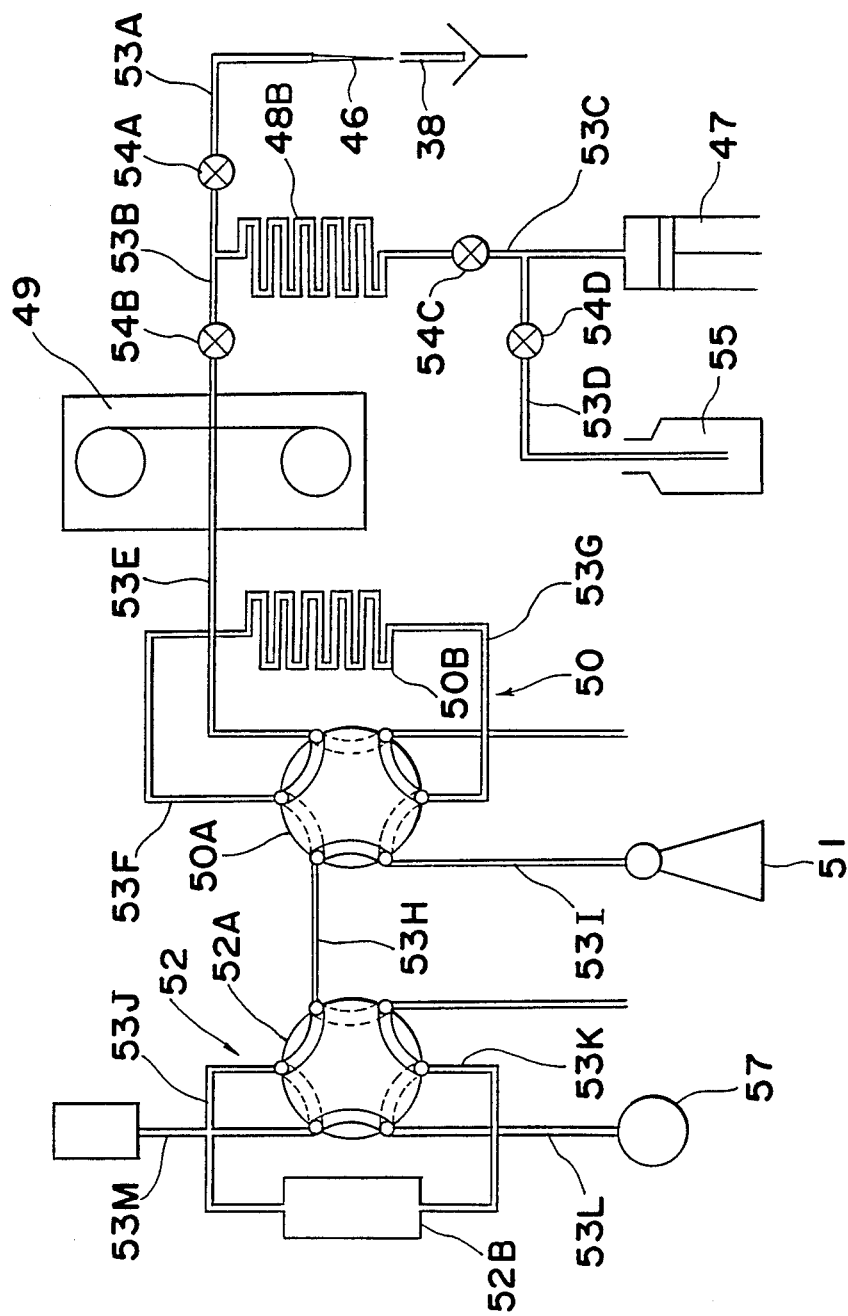
FIG. 19 is a schematic diagram of the filtration, concentration and injection apparatuses shown in FIG. 3.

The respective apparatuses are connected through the respective coupling passages 53A through 53M as shown in FIG. 19. Electromagnetic valves 54A through 54D are disposed on the coupling passages 53A through 53D. In FIG. 20, a water storage vessel 55 is sucked by the syringe pump 47, and the sample mixture is injected into the analytic column from the six-way valve 52 with a concentration column on it by the analytic pump.

The operation of the present apparatus is effected with a control panel 56, shown in FIG. 20, disposed on the upper portion. In FIG. 20, a power switch 57 is provided, and a switch 58 may set the time, which is required to guide the sample into the concentration column 52B from the sampling loop 50B. Switch 58 may be set at an interval of one minute. A switch 59 for setting the analytic time may enter the conditioning of the concentration column automatically after the analytic time to prepare for the next analysis. A switch 60 may set the washing frequency of the passage. A manual, automatic change-over switch is operated in such a manner that, when the operation is switched into the manual one, the manual operations such as the vertical operation of the syringe, passage washing, filter paper feeding, water pump starting and stopping, six-way valve switch and so on may be performed by the button depicted as (●) in the drawings. In the drawing, ( ⊙ ) is a start button during the automatic operation, and (⊙) is a contact button for transmitting the signals to the external apparatus.

Figure 21:
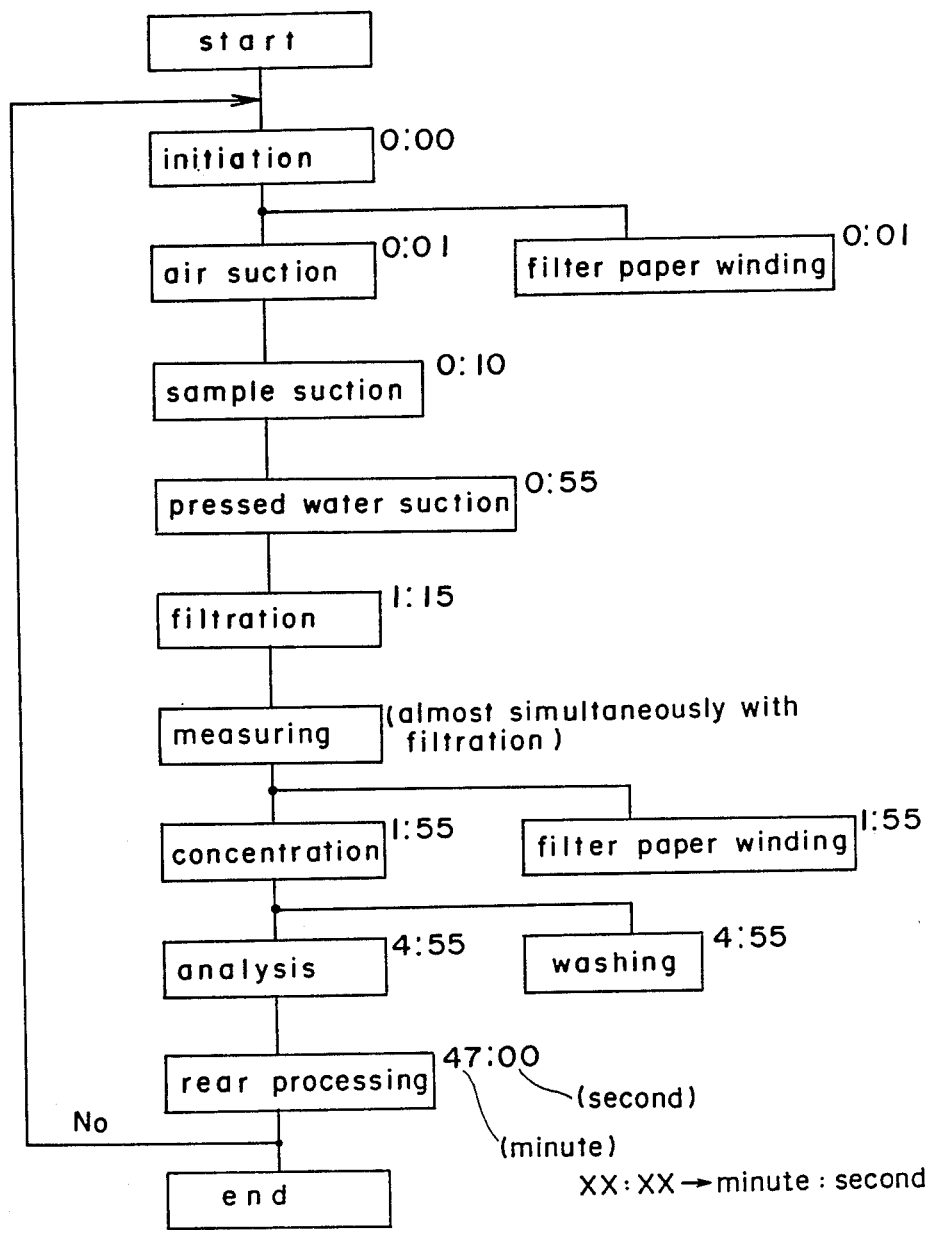
FIG. 21 is a flow chart of the operation sequence of the filtration, concentration and injection apparatuses.

The FCI is operated in the order shown in the block diagram of FIG. 21, which operation will be described hereinafter.

First, the reaction tube 38 with the reaction mixture in it is grasped by the robot 20 and is placed under the sampling nozzle 46. The sample nozzle 46 is lowered and is put into the reaction tube 38. At the same time, the electromagnetic valve 54C disposed on the interlocking passage 53C between the loop 48 for capacity adjusting operation and the syringe pump 47 is closed and the electromagnetic valve 54D on the interlocking passage 53D between the water storage vessel 55 and the syringe pump 47 is opened to suck an optional amount of water into the syringe pump 47. Then, the electromagnetic valve 54D is closed, the electromagnetic valve 54A and the electromagnetic valve 54C disposed on the interlocking passage 53A between the loop 48 for capacity adjusting operation and the sampling nozzle 46 are opened to such a constant amount of the reaction mixture in the reaction tube 38 from the sampling nozzle 46 to guide it into the loop 48 for capacity adjusting operation. After the suction of a small amount of air, the electromagnetic valve 54A is closed and the electromagnetic valve 54B disposed on the interlocking passage 53B between the loop 48 for capacity adjusting operation and the filtration unit 49 is opened to guide the reaction mixture in the loop 48 for capacity adjustment into the six-way valve 50 with a sampling loop on it through the filtration unit 49 by the syringe pump 47. In the filtration unit 49, the roll-shaped filter paper of 0.45 μm in hole diameter is continuously wound to filter the sample diameter. The reaction mixture which has been guided into the six-way valve 50 with a sampling loop on it is guided into the sampling loop 50B through a solid-line circuit in the drawing of the six-way valve 50A and the interlocking passage 53F. Continuously the six-way valve 50A is switched into a dot-line circuit to introduce the water of the water pump 51 into the sampling loop 50B through the interlocking 53I, the dot-line circuit of the six-way valve 50A and the interlocking passage 53G to introduce the reaction mixture in the sampling loop 50B into the six-way valve 52 with the concentration column on it through the interlocking passage 53F, the dot-line circuit of the six-way valve 50A and the interlocking passage 53H. In the six-way valve 52 with the concentration column on it, it is introduced into the concentration column 52B through the solid-line circuit of the six-way valve 52A, the interlocking passage 53J and is adsorbed into the concentration column 52B. After the optional time, the six-way valve 52A is switched into the dot-line circuit to feed the eluate into the concentration column 52B through the interlocking passage 53L, the dot-line circuit of the six-way valve 52A, and the interlocking passage 53K to inject the reaction mixture in the concentration column 52B into the analytic column through the interlocking passage 53J, the dot-line circuit of the six-way valve 52A and the interlocking passage 53M to perform the separation and quantitative functions.

The operation is performed under the conditions of 3.9 in PH, 240 nm in wave length, 1 ml per minute in flow speed with acetonitrile:methanol:water:acetic acid = 350:150:250:1 as the eluate.

After the constant time, the water is introduced into the respective six-way valves 50A, 52A from the water pump 51 through the six-way valve 50A with the sampling loop on it being provided as the dot-line circuit, and through the six-way valve 52A with the concentration column on it being provided as the solid-line circuit to perform the washing operation of the flow passage in the valve and of the concentration column 52B. Also, at the same time the syringe pump 47 is operated to wash the sampling needle 46 and the sampling loop 48.

In a series of operations, the water by the syringe pump 47, the reaction mixture by the sample nozzle 46 and the suction amount of the air are optionally varied by the dip switch of the electric circuit.

Figure 22:
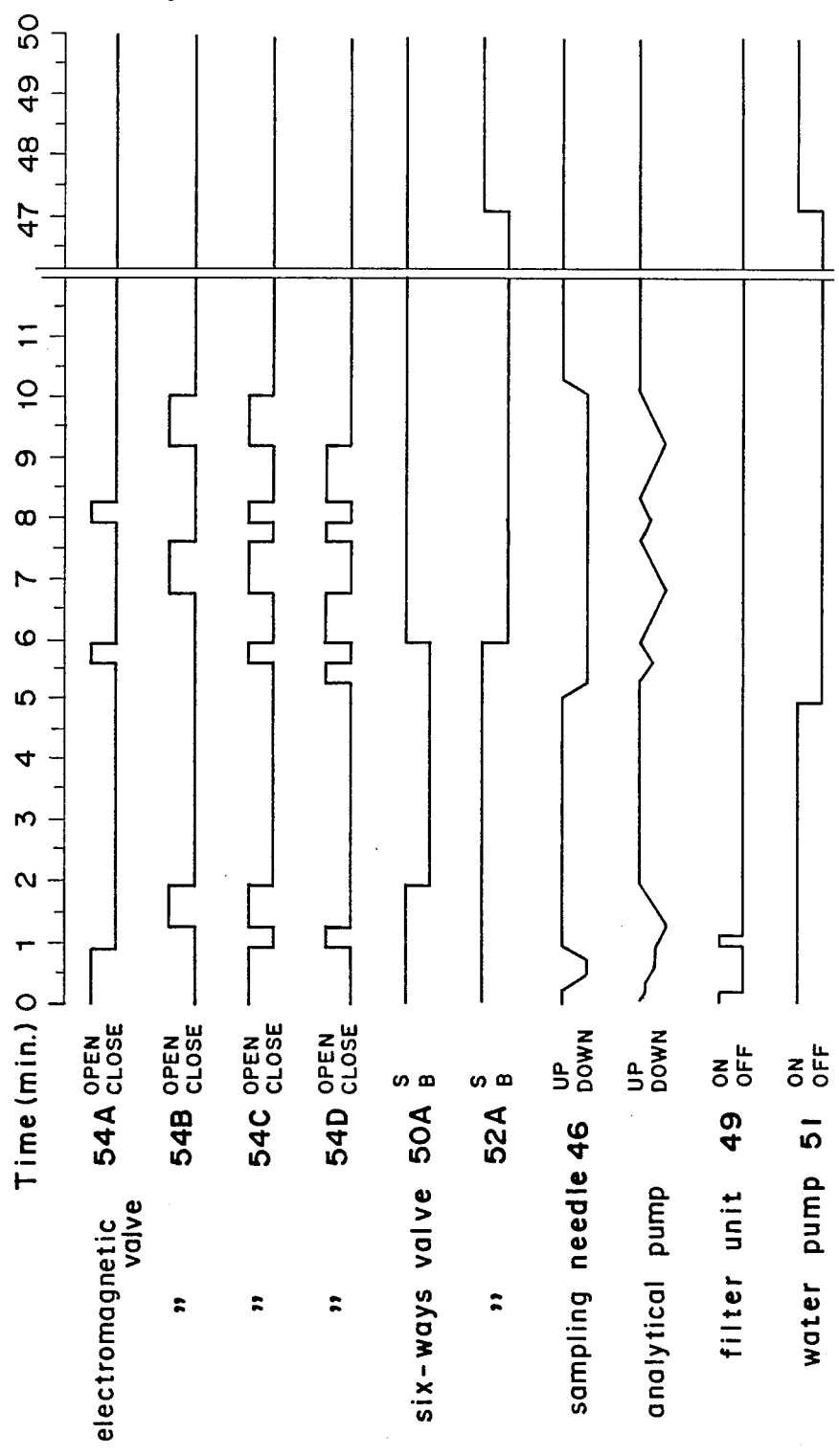
FIG. 22 is an operation circuit diagram of each apparatus.

The representative operation cycles of the electromagnetic valves 54A through 54D, the six-way valved 50A, 52A, the sampling nozzle 46, the syringe pump 47, the filter unit 49, and the water pump 51 are shown in FIG. 22. An operation time of up to two minutes is required for the sampling of the sample, and five minutes for the washing operation (twice) of the flow passage.

When it is injected into the HPLC by the above described FCI, the analysis operation is performed by the predetermined, constant programmed HPLC.

However, the column to be used in the HPLC uses YMCA-312 (ODS), the eluate A uses 90% acetonitrile, the eluate B uses acetonitrile/methanol/water/acetic acid (1400:800:900:4).

The results of the HPLC are input into the data processer (not shown) through the digitalization of the analog signals by the A/D converter. The data processor performs the waveform processing, content calculation, re-processing and re-calculation of the improper waveform processing, memory of the chromatogram and calculation results, preparation of the reports with the inhibition, $IC_{50}$ and so on described on them, and the preparation of the data transfer to the upper computer.

Experiment of the Adsorption Conditions onto the Concentration Column (I) Each (1 mg per ml solution) of leukotriene $B_4$ (LTB$_4$), hydroxyeicosatetraenoic acids (HETEs) are diluted with water into 200 times, thus resulting in a suction amount of 1.5 ml, sampling loop 1 ml. The flow speed of the water pump 51 and the switching time of the six-way valve 52A are varied to examine their influences on the chromatogram.

When the pump flow speed is 1 ml per minute, the constant peak height is shown at 4 minutes or more in switching time but it becomes smaller in proportion to the switching time at 3 minutes or less. The peak height is constant at 2 minutes or more when the pump flow speed is 1.5 ml and 2 ml per minute. When it is 3 ml or more per minute, the concentration column 52B is short and the pressure loss is low. Thus, there are some fears of detrimental influences on the adsorption which are not investigated. The switching time of the six-way valve 52A is 2 minutes at 2 ml per minute in the pump flow speed in the adsorption onto the concentration column 52B of the sample mixture.

Figure 23A:
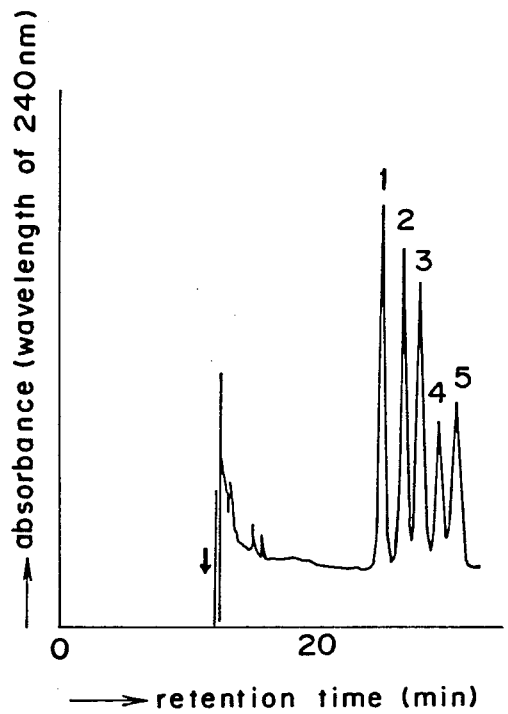
FIGS. 23 (A), (B), (C) and FIG. 24 show chromatograms of various kinds of sample solutions.
Figure 23B:
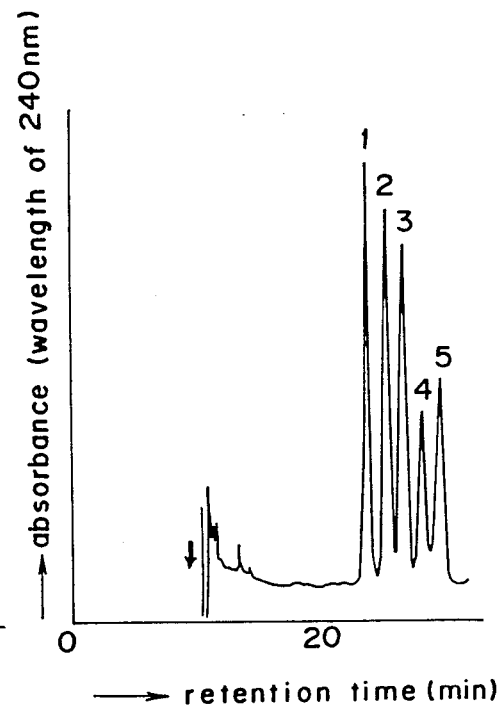
Figure 23C:
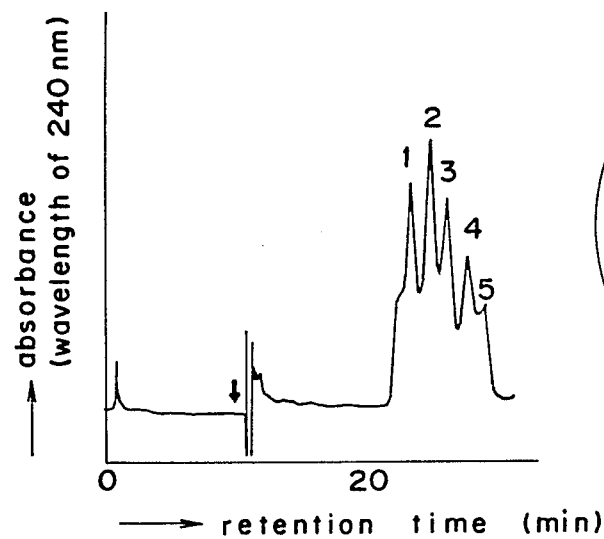
Figure 24:
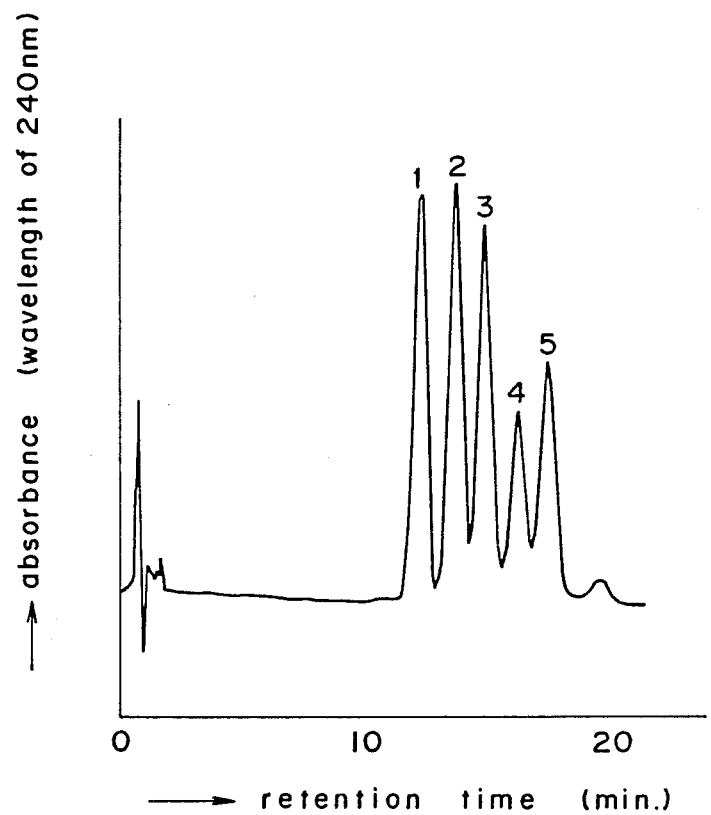

(II) The influences of the ethanol concentration in the reaction mixture on the adsorption onto the concentration column are investigated. The $LTB_4$ and HETEs (each 1 mg per ml) are diluted with ethanol into 10 times. The ethanol 0, 0.1, 0.4, 0.9, 1.2 and 1.9 ml is added into this solution 0.1 ml and is produced into 2 ml with water to provide reaction mixture (ethanol concentration 5, 10, 25, 67, 100%), so that the peak height of the HPLC, and the shape are investigated. FIG. 23(a) shows the chromatogram of 5% ethanol concentration, FIG. 23(b) one of 50%, FIG. 23(c) one of 67%. The chromatogram of 5% and 50% is almost the same in both the peak height and the shape with the influences of the ethanal being not recognized, but in 67%, the peak overlaps and becomes broad so that the normal peak can not be provided. FIG. 24 shows the chromatogram provided in a case where the $LTB_4$ and the HETEs (each 1 mg per ml) are diluted with water into 5 times and is directly injected at 50 μl into HPLC (UV240nm). As compared with FIG. 23(b), it is found out that the peak separation degree remains without any change, and the on-line of the FCI has no influences upon the chromatogram in 50% or less in ethanol. This is similar to a case where acetonitrile is used.

Experiment of Filter-Paper Selection

The influences of the filter area and the hole diameter on the filtration are investigated.

The 50% ethanol suspension (cells $5 \times 10^7$ per ml) of the RBL-1 is moved through the membrane filter of cellulose nitrate, cellulose acetate mixture type different in diameter and hole diameter at 1 ml per minute in filtrating speed, so that the turbidity and the filter paper clogging are investigated after the passing. A filter paper of 13 mm in diameter causes a sudden pressure rise because of clogging at 0.6 through 0.7 ml. A smooth filter operation is performed at 25 mm and 47 mm. A filter paper of 25 mm in diameter causes clogging at 1.5 ml. Also, clogging is caused at 0.3 through 0.5 ml with a hole diameter of the filter paper being 0.22 μm, but easy filtering operation is performed at 0.45 μm or more. However, at 1.2 μm, turbidity is caused in the passing solution.

Then, the influence of the material used in the filter paper on the chromatogram is investigated. The HPLC is performed after the passage of the filtration/concentration apparatus with 50% ethanol suspension (cells $5 \times 10^7$ per ml) of the RBL-1 being the sample solution. A filter paper of 0.45 through 0.6 μm in hole diameter, 25 mm in diameter is used. Also, the sample solution is centrifuged (2500 rpm, ten minutes) and the supernatant is used for the control. The filter paper is 0.45 μm in hole diameter of the RC of a reproduction cellulose type, 25 mm in diameter, filter area. Although leakage from the filter paper can hardly be recognized in the case of water, a large amount of leakage can be recognized in the case of the 50% ethanol.

Precision and Comparison Experiment with the Conventional Method

The $LTB_4$ and HETEs (each 1 mg per ml) are diluted into 10 times with ethanol. The ethanol 0.9 ml is added into this solution to provide 2 ml, with water, as the sample solution. It is injected into the FCI to perform the HPLC. Accuracy is repeatedly obtained from the peak height provided. The accuracy as good as 0.4 through 1.7% in coefficient of variation as shown in the following Table 1.

TABLE 1

| | Peak Height (mm) | | | | | |
|---|---|---|---|---|---|---|
| Times | $LTB_4$ | 15-HETE | 11-HETE | 8- and 12-HETE | 9-HETE | 5-HETE |
| 1 | 52.8 | 94.8 | 93.2 | 80.3 | 40.8 | 50.6 |
| 2 | 54.0 | 95.7 | 97.5 | 80.8 | 41.5 | 51.9 |
| 3 | 53.1 | 95.3 | 95.0 | 80.4 | 41.2 | 50.9 |
| 4 | 54.7 | 95.5 | 96.3 | 80.5 | 41.0 | 51.0 |
| 5 | 54.4 | 94.7 | 94.2 | 79.8 | 40.9 | 50.8 |
| 6 | 54.2 | 94.6 | 94.3 | 80.4 | 41.0 | 50.9 |
| Mean | 53.9 | 95.1 | 95.1 | 80.4 | 41.1 | 51.0 |
| Standard Deviation | 0.75 | 0.46 | 1.57 | 0.33 | 0.25 | 0.45 |
| Coefficient of Variation | 1.39 | 0.48 | 1.65 | 0.41 | 0.69 | 0.89 |

In the Table 1, UV 240 nm is employed to measure except for $LTB_4$. Also, the present method is conformed to the conventional method, in accordance with the investigation, by the use of RBL-1, of the interference of 5-lipoxygenase of unique raising interference agent 2-(12-hydroxy-dodeca-5,10-diynyl)-3,5,6-trimethyl-1,4-benzoquinone (AA-861).

The injection amount of the reverse phase HPLC using the column of 4 through 4.6 mm in inner diameter is 50 through 100 μl at limit. Though influences hindering separation are feared in the method of injecting the sample mixture 1 ml into the pre-column to introduce it into the analytic column, no influences are recognized even at 50% ethanol as shown in FIG. 24(b). The concentration method by the pre-column is the same as the case where 1 ml is injected directly into the HPLC, so that the concentration of 10 through 20 times may be performed under the on-line. Also, the repeating accuracy is better with the results at the AA-861 is conformed to the conventional method.

Figure 25A:
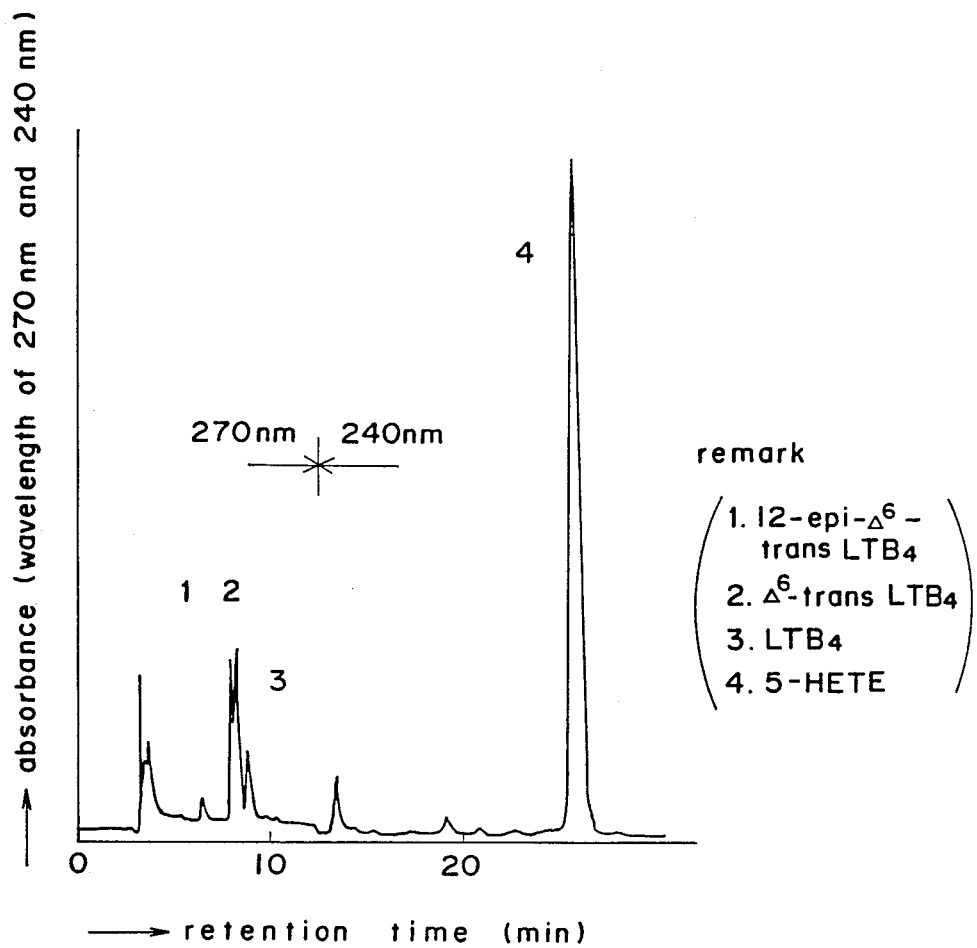
FIGS. 25(A) and (B) show chromatograms obtained by using this apparatus.
Figure 25B:
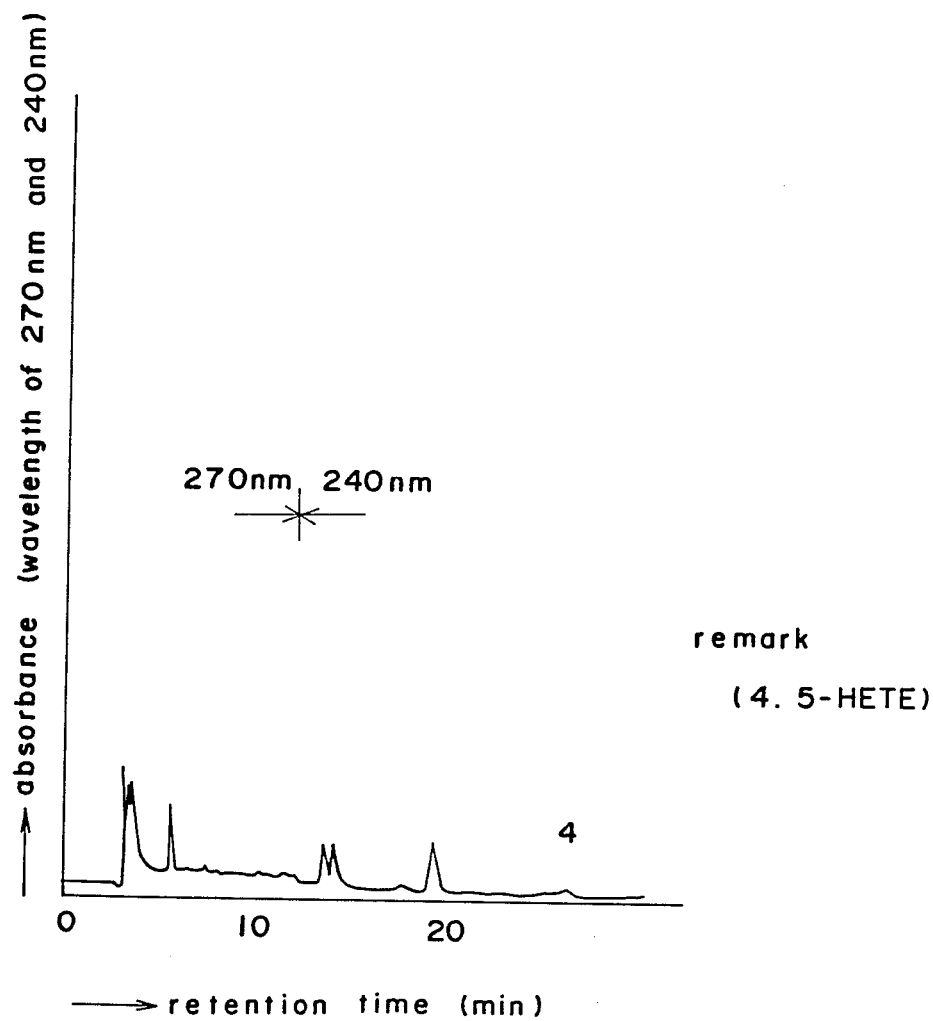
Figure 27:
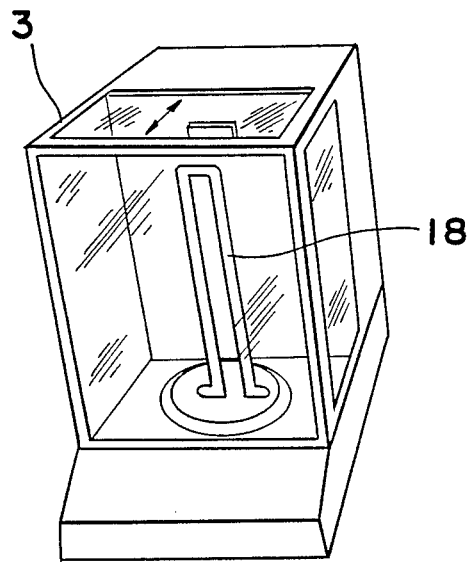
FIG. 27 is a perspective view of the electronic balance.
Figure 28:
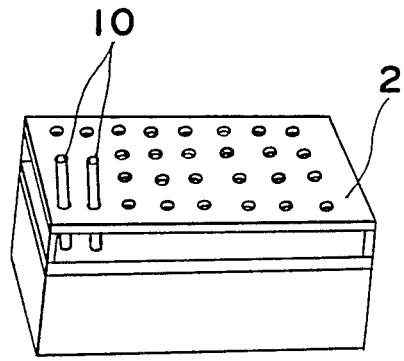
FIG. 28 is a perspective view of the rack.
Figure 29:
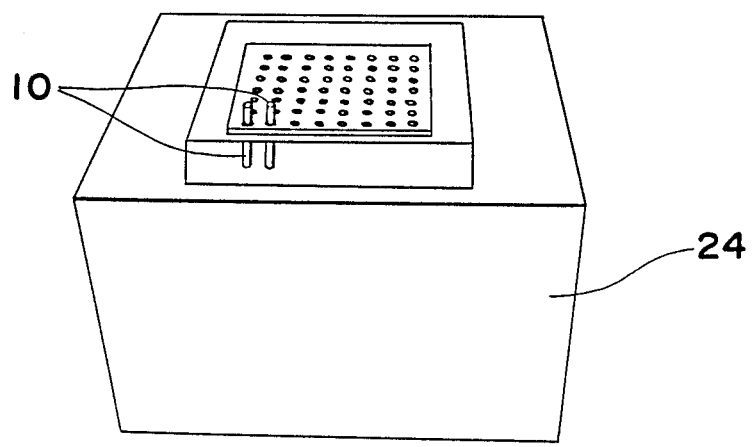
FIG. 29 is a perspective view of the incubator.

Chromatograph Operated in Accordance With Operation System With the Use of the Present Invention Apparatus, and Comparison Experiment Results in the Conventional Manual Method The chromatogram obtained through the operation by the use of the RBKI-1 cell, and the chromatogram of the case where the AA-861 is $10^{-6}M$ added are shown in FIG. 25. The chromatogram by the manual method of the $LTB_4$ and the HETE isomer is shown in FIG. 26. The references 1, 2, 3, 4 of FIG. 25 come from FIG. 26. Although the retention time of the automatic method and the manual method remain unchanged, the number of the theoretical plates showing the column performance is 11500 (stage/column) with automation in 5-HETE, 8100 in the manual method. The number of the theoretical plates in the automatic method is larger, because of the time control for the valve switching operation improved through the automation, the concentration column and the analytical column. The repeating accuracy is improved by about one half, $LTB_4$ 3.5%, 5-HETE 4.0%, in the coefficient of variation as compared with the manual method. The reason why the coefficient of variation is improved is that the time for the reaction, the injection and so on becomes correct through the automation, as does the injection liquid amount. Also, the time for requiring the pretreatment is shortened into one hour and twelve minutes through one hour and sixteen minutes, about ⅓ of the manual method in the number of the largest samples (primary assay 24, the secondary assay 12, number of the processings 61), thus saving a large amount of time. Although the operation analyzes the lipoxygenase reaction by the use of RBL-1 cell, rate platelets, instead of the RBL-1 cell, are used in the analysis of the cyclooxygenase reaction. The rat platelets are prepared so that the platelets concentration may become $1 \times 10^9$ call per ml by drawing blood from the rate abdominal aorta with the use of 3.2% sodium citrate and centrifuging it at the room temperature.

The analysis of the cyclooxygenase reaction is similar to the analysis of the lipoxygenase reaction. The prepared platelets are added into the reaction tube 16 from the dispenser 6. Namely, the platelets of 0.25 ml are added to the diluted sample of 10 $\mu$l in the reaction tube 16. After the reaction mixture is preincubated for 5 minutes, arachidonic acid of 125 $\mu$g per 25 $\mu$l is added from the dispenser 7 to incubate for 15 minutes and the reaction is stopped through the injection of the ethanol 1.0 ml from the dispenser 8.

Though any enzyme can be used in the present reaction, particularly preferable is an enzyme which shows biological activity when the substrate of the enzyme or the product of the reaction is a small amount. For example, the lipoxygenase or the cyclooxygenase enzymes as preferable, where the products are leukotrienes, prostaglandins, thromboxanes. As for the enzyme preparation, such tissue cells as described in the embodiment may be used in addition to purified enzymes.

As is clear from the above-described description, according to the automatic apparatus of the present invention, savings are provided, and the time may be considerably shortened to ⅓ of that of the conventional manual operation because of the automation of the operation from the pretreatment step to the data processing and the analysis steps. Also, the coefficient of variation is reduced by ½ in the accuracy of the measurement value as compared with the conventional manual method because of the more correct injection amount or the like.

Also, each member of this apparatus has the following effects.

1. As the robot may be used like the human hand, all the complicated operations may be performed, and the varied operation may be simply performed. Particularly, the use of the horizontal multi-joint type robot allows for faster speed, better precision, wider action range and simplifies easier assembling of the multiple-object operation method.

2. In the automatic weighing and dissolution apparatus, the sample tube is grasped and moved with the chuck of the robot. In the automatic dilution and reacting apparatus, the nozzle holder is grasped and carried with the chuck of the robot, but the sample tube and the reaction tube are not moved, so that the respective time may be shortened, and particularly the speed of the time for the enzyme reaction may be improved.

3. As for the various types of dispensers, an automatic dispenser composed of a digital diluter/pipetter is used, so that the addition, dilution, sampling and injection of the solvent operations may be performed in shorter time and with better precision.

4. The washing operation within the nozzle is effected simultaneously with the injection of the diluted solution in the automation dilution and reacting apparatus; however, the washing operation of the nozzle is not required to be effected for each of the samples. When the washing is required, the washing may be performed with better efficiency, because the washing vessel may be formed integrally with the nozzle stand.

5. As the stirring is performed by one magnetic stirrer with a rotor being kept in advance in the reaction tube in the automatic reaction apparatus, the stirring of a plurality of reaction tubes of up to 64 may be performed at one time.

6. As the filtration, the concentration, and injection operations into the HPLC of the reaction mixture are performed with full automation using the on-line system, the operation time may be considerably shortened. Also, the quantitative property is improved through the automation, thus resulting in better accuracy of 0.4 through 1.7% in coefficient of variation. In accordance with this invention, the sample mixture is filtered by the filtration system, instead of the centrifugation system. As the filter paper continuous winding system is adopted, it is suitable for the on-line system so that the equipment expenses may be reduced. In addition, as the milli-pore filter of 0.45 $\mu$m is used for the filter paper, the filtration at the HPLC becomes unnecessary. The operation for evaporation of the sample mixture may be made unnecessary through the passing operation through the six-way valve with the concentration column on it prior to the analytical column. Besides, using the concentration column, a concentration 10 times through 20 times as many as the conventional one may be performed, and the repeating accuracy may be good, thus resulting in various advantages.

Although the present invention has been fully described by way of example with reference to the accompanying drawings, it is noted that various changes and modifications will be apparent to those skilled in the art. Therefore, unless such changes and modifications depart from the scope of the present invention, they should be construed as being included herein.

What is claimed is:

1. An apparatus for automatically analyzing the effect of a sample on an enzyme, said apparatus comprising:
   weighing means for weighing a sample;
   dissolving solvent adding means for adding solvent to the sample;
   dissolving means for facilitating the dissolution of the sample in the solvent to produce a sample solution;
   dilution solvent adding means for adding solvent to the sample solution to produce a diluted sample solution;
   diluted sample solution pipetting means for injecting at least a portion of the diluted sample solution into a reaction tube;

enzyme adding means for adding an enzyme into the reaction tube into which the diluted sample solution is injected by said diluted sample solution pipetting means;

substrate adding means for adding a substrate of the enzyme into the reaction tube to obtain a reaction mixture in which an enzyme reaction takes place;

a preservation vessel for preserving the reaction mixture;

moving means for moving the reaction tube into said preservation vessel to preserve the reaction mixture;

filtering means for filtering the reaction mixture as preserved by the preservation vessel to produce a filtrate of the reaction mixture;

concentrating means for concentrating the filtrate to produce a concentrated filtrate of the reaction mixture;

analysis means for producing data based on an analysis of the concentrated filtrate of the reaction mixture;

filtrate injecting means for injecting the concentrated filtrate of the reaction mixture into the analysis means to allow the analysis means to produce data based on the analysis of the concentrated filtrate;

data processing means for processing the data based on the analysis of the concentrated filtrate into information indicative of the effect of the sample on the enzyme reaction; and control means operatively connected to said dissolving and said dilution adding means, said sample solution pipetting means, said enzyme adding means, said substrate adding means, said moving means and said filtrate injecting means for automatically controlling the adding of the solvent by said dissolving solvent adding means and by said dilution solvent adding means, the injection of the diluted sample solution by said diluted sample solution pipetting means, the adding of the enzyme by said enzyme adding means, the adding of the substrate by said substrate adding means, the movement of said moving means, and the injection of the concentrated filtrate by said filtrate injecting means.

2. An apparatus according to claim 1, wherein said weighing means is an electronic balance, said dissolving solvent adding means is a solvent dispenser connectable to a source of solvent for dispensing solvent, said dissolving means is a dissolution vessel having an ultrasonicator, and further comprising a sample rack for supporting sample test tubes containing the sample, and a first robot having a movable arm equipped with a chuck, said control means operatively connected to said first robot for controlling said robot to grasp a sample tube supported by said sample rack with said chuck, and to sequentially move the grasped sample tube, via said movable arm, onto said electronic balance, to said solvent dispenser and to said dissolution vessel;

wherein said dilution solvent adding means is a dilution dispenser including a dilution nozzle connectable to a source of solvent for dispensing solvent therefrom, said diluted sample solution pipetting means is a sample pipetter for pipetting diluted sample solution, said enzyme adding means is an enzyme dispenser including an enzyme injection nozzle connectable to a source of enzyme for dispensing enzyme therefrom, said substrate adding means is a substrate dispenser including a substrate injection nozzle connectable to a source of substrate for dispensing substrate therefrom, said preservation vessel includes a preservation rack for supporting a plurality of said reaction tubes, said moving means is a second robot including a chuck, and further comprising a dilution rack for supporting a plurality of sample tubes, and an incubator including an incubation rack for supporting a plurality of reaction tubes, said control means operatively connected to said second robot for controlling said second robot to grasp said dilution nozzle with the chuck thereof and move the same to said dilution rack, to grasp said sample pipetter with the chuck thereof and move the same between said dilution rack and said incubator rack, to grasp said enzyme injection nozzle with the chuck thereof and move the same to said incubator rack, to grasp said substrate injection nozzle with the chuck thereof and move the same to said incubator rack, and to grasp the reaction tubes supported by said incubator rack and move the same to said preservation rack; and wherein said filtering means includes a web of filter material, a supply means from which said filter material is supplied, a take-up reel for receiving the filter material from said supply means and means for continuously winding said filter material around said take-up reel, said concentrating means is a concentration column for absorbing the filtrate, said concentration column connected to said analysis means, and said filtrate injecting means comprises a valve operatively connected between said concentration column and an eluting source of solvent, said valve movable to a position at which said eluting source of solvent is open to said concentration column for allowing the solvent, from said eluting source, to pass through said concentration column to elute the filtrate absorbed thereby and to force the eluted filtrate into said analysis means connected to said concentration column.

3. An automatic weighing and dissolution apparatus for automatically weighing and dissolving a sample with a solvent, said apparatus comprising:

a sample rack for supporting a plurality of sample tubes containing a sample;

an electronic balance;

solvent adding means for dispensing solvent;

a dissolution vessel for facilitating the dissolution of the sample in the solvent dispensed by said solvent adding means;

a robot having a movable arm including a chuck; and a computer operatively connected to said electronic balance, said solvent adding means, said dissolution vessel and said robot for controlling said robot to move a sample tube supported by said sample rack to said electronic balance and to the solvent adding apparatus once weighed by said electronic balance, for controlling said solvent adding means to dispense an amount of solvent based on the weight of the sample contained in the sample tube, for controlling the robot to transfer the sample tube to said dissolution vessel once the solvent is added by said solvent adding means, and for controlling the operation of said dissolution vessel once the sample tube has been transferred thereto by said robot.

4. An apparatus according to claim 3, wherein the movable arm of said robot is displaceable along a horizontal plane and has a plurality of points about which portions of said movable arm are pivotable.

5. An apparatus according to claim 3, wherein said solvent adding means includes a plurality of dispensers for dispensing a plurality of different types of solvents, respectively.

6. An apparatus according to the claim 3, wherein said dissolution vessel includes a heater comprising an ultrasonicator, said computer operatively connected to said heater for controlling the operation of said heater.

7. An automatic dilution and reacting apparatus for diluting a sample solution and facilitating an enzyme reaction within said sample solution, said apparatus comprising:

a dilution rack for supporting a plurality of sample tubes containing a sample solution;

a dilution dispenser including a dilution nozzle mounted on flexible piping and connectable to a source of solvent for dispensing solvent therefrom, and a dilution nozzle stand for supporting the dilution nozzle;

an incubator, said incubator having support means for supporting a plurality of reaction tubes therein;

a sample pipetter having a pipetter nozzle and a pipetter stand for supporting said pipetter nozzle;

a plurality of different reaction mixture dispensers for dispensing different components of a reaction mixture;

each of said reaction mixture dispensers including a reaction nozzle mounted on flexible piping and connectable to a respective source of the components, and reaction nozzle stands for supporting said reaction nozzles;

at least one washing vessel for rinsing at least one of said nozzles;

a robot having a movable arm including a chuck; and a controller operatively connected to said robot for controlling said robot to grasp said nozzles with said chuck and move the same between said stands and said racks, respectively, and to said at least one washing vessel, in a manner in which the sample solution is diluted in the sample tube supported in said dilution rack by solvent dispensed by said dilution dispenser via said dilution nozzle grasped by said robot and moved to said sample rack to produce diluted sample solutin, the diluted sample solution is withdrawn from the sample tubes by said sample pipetter and is dispensed thereby into the reaction tubes supported by said support means of said incubator, and the components of the reaction are dispensed into said reaction tubes via said reaction nozzles grasped by said robot and moved to said support means of said incubator.

8. An apparatus according to claim 7, and further comprising a preservation vessel for preserving the reaction mixture after the reaction components are introduced into the reaction tubes, said controller further controlling said robot to grasp said reaction tubes supported by said support means of said incubator, once the reaction components are introduced therein, and to move the reaction tube to said preservation vessel.

9. An apparatus according to claim 7, wherein the movable arm of said robot is displaceable along a horizontal plane and has a plurality of joints about which portions of said movable arm are pivotable.

10. An apparatus according to claim 7, wherein each of said dispensers comprises a digital diluter pipetter, each said flexible piping comprises a coil-shaped teflon tube, and said nozzles are integral with said teflon tubes at tip ends thereof, respectively.

11. An apparatus according to claim 7, wherein said incubator includes a magnetic stirrer for stirring the reaction mixture contained in reaction tubes supported thereon by said support means.

12. An apparatus according to claim 7, wherein said reaction mixture dispenser comprises a plurality of independent dispensers each having a said reaction nozzle and each connectable to a respective one of the sources of the components, and said controller further controls said robot to sequentially grasp and move the nozzles of said independent dispensers to said support means of said incubator during predetermined time intervals.

13. An apparatus according to claim 7, wherein said reaction mixture dispenser is a reaction mixture dispenser for dispensing at least enzyme solution.

14. An automatic filtration/concentration/injection (FCI) apparatus for filtering a solution to produce a filtrate, concentrating the filtrate to produce a concentrated filtrate, and injecting the concentrated filtrate to facilitate the analyis thereof, said apparatus comprising:

a sampling nozzle, and a syringe pump operatively connected to said sampling nozzle for drawing at least a portion of a reaction mixture through said sampling nozzle;

a filter unit disposed in the apparatus downstream of said sampling nozzle for filtering the reaction mixture drawn through said sampling nozzle;

said filter unit including filter paper, a supply means from which said filter paper is supplied, a take-up reel for receiving the filter from said supply means and means for continuously winding said filter paper around said take-up reel;

a first valve connected to a sampling loop and disposed in the apparatus downstream of said filter unit for receiving a predetermined volume of filtrate passing through said filter paper;

a concentration column for adsorbing the filtrate and disposed in the apparatus downstream of said first valve and said sampling loop;

a water pump operatively connected in the apparatus for pumping water and the filtrate in said sampling loop through said concentration column;

an analytical column for analyzing the reaction mixture and connected to said concentration column; and eluting means for eluting the filtrate adsorbed in said concentration column and allowing the eluted filtrate to pass into said analytical column.

15. A method for automatically analyzing the effect of a sample on an enzyme, comprising the steps of:

weighing a sample, adding a solvent to the sample, dissolving the sample in the solvent to produce a sample solution, dispensing further solvent to at least a portion of the sample solution to produce a diluted sample solution, pipetting at least a portion of the diluted sample solution into a reaction tube, dispensing enzyme and substrate of the enzyme into the reaction tube containing diluted sample solution to produce a reaction mixture, moving the reaction tube into a preservation vessel capable of preserving a reaction to preserve the reaction mixture, filtering the reaction mixture as preserved by the preservation vessel to produce a filtrate, concentrating the filtrate to produce a concentrated filtrate of the reaction mixture, injecting the concentrated filtrate into an analysis apparatus capable of analyzing solution to produce data based on the analysis of the concentrated filtrate, and processing the data based on the analysis of the concentrated filtrate into information indicative of the effect of the sample on the enzyme, wherein all the steps are performed automatically.

16. A method according to claim 15, wherein the steps of weighing the sample, adding solvent to the sample, and dissolving the sample in the solvent are automatically performed with a weighing and dissolution apparatus by grasping a sample tube supported in a sample rack with a chuck provided on a movable arm of a first robot, moving the sample tube to an electronic balance, moving the sample tube to a solvent adding apparatus, dispensing an amount of solvent into the sample tube from the solvent adding means based on the weight of the sample contained in the sample tube, moving the sample tube to a dissolution vessel capable of facilitating dissolution of the sample in the solvent after the addition solvent to the sample tube to produce a sample solution, and moving the sample tube containing the sample solution to a dilution rack in a dilution and weighing apparatus;

wherein the steps of dispensing further solvent to at least a portion of the sample solution, pipetting at least a portion of the diluted sample solution into a reaction tube, dispensing enzyme and substrate into the reaction tube, and moving the reaction tube into a preservation vessel are automatically performed with a dilution and reacting apparatus by grasping a nozzle of a dilution dispenser with a chuck of a second robot, moving the nozzle of the dilution dispenser to the sample tube supported in the dilution rack, dispensing solvent from the dilution dispenser through the nozzle thereof to at least a portion of the sample solution to produce a diluted sample solution, grasping a sampling pipetter with the chuck of the second robot, pipetting at least a portion of the diluted sample solution with said sampling pipetter into a reaction tube supported in a reaction tube rack in an incubator, grasping each respective nozzle of a plurality of reaction mixture dispensers for dispensing enzyme and substrate necessary for an enzyme reaction with the chuck of the second robot, moving sequentially each of the nozzles of the reaction mixture dispensers to the reaction tube containing the diluted sample solution, dispensing enzyme and substrate into the reaction tube from the reaction mixture dispensers and through the nozzle thereof at predetermined time intervals to produce a reaction mixture, grasping the reaction tube with the chuck of the second robot, moving the reaction tube into a preservation vessel capable of preserving the reaction mixture, grasping the reaction tube in the preservation vessel, and moving the reaction tube, once the reaction mixture is preserved, to a sampling nozzle of a filtration/concentration/injection apparatus capable of withdrawing at least a portion of the reaction mixture from the reaction tube;

wherein the steps of filtering the reaction mixture, concentrating the filtrate, and injecting the concentrated filtrate into an analysis apparatus are automatically performed with the filtration/concentration/injection apparatus by drawing from the reaction tube at least a portion of the reaction mixture through the sampling nozzle into the filtration/concentration/injection apparatus, filtering the reaction mixture drawn through the sampling nozzle with a filter unit disposed in the apparatus downstream of the sampling nozzle to obtain a filtrate, concentrating the filtrate by adsorbing at least a portion of the filtrate on a concentration column disposed in the apparatus downstream of the filter unit, eluting the filtrate adsorbed on the concentration column from said column with an eluting solvent to obtain a concentrated filtrate, injecting the concentrated filtrate eluted from the concentration column into an anaylsis column of a high pressure liquid chromatograph disposed in the apparatus downstream of the concentration column to produce data based on the analysis of the concentrated filtrate, and wherein the steps performed by the first and second robots are automatically controlled by a computer.

17. A method according to claim 15, wherein said step of dispensing enzyme comprises dispensing lipoxygenase.

18. A method according to claim 15, wherein said step of dispensing enzyme comprises dispensing cyclooxygenase.

19. A method according to claim 15, wherein said step of dispensing enzyme comprises dispensing lipoxygenase or cyclooxygenase, and said step of dispensing substrate comprises dispensing arachiodonic acid, and further comprising a step of dispensing ethanol.

20. A method of automatically weighing and dissolving samples, comprising grasping a sample tube retained in a sample rack with a chuck provided on a movable arm of a first robot, moving the sample tube with said robot to an electronic balance, moving the sample tube with said robot to a solvent adding apparatus, dispensing an amount of solvent into the sample tube based on the weight of the sample contained in the sample tube, moving the sample tube with said robot to a dissolution vessel capable of facilitating the dissolution of the sample in the solvent after the addition of solvent to the sample tube to produce a sample solution, and moving the sample tube containing the sample solution with said robot to a dilution rack in a dilution and weighing apparatus, wherein the operation of said robot, the determining of the amount of solvent to add to the sample based upon the weight of the sample, the adding the solvent into the sample tube, the operation of the electronic balance, the operation of the solvent adding apparatuses, and in the operation of the dissolution vessel are automatically controlled by a control means.

21. A method of diluting and reacting a sample, comprising grasping with a chuck of a robot a dilution nozzle connectable to a dilution dispenser with a flexible tube, moving the dilution nozzle with said robot to a sample tube containing a sample solution supported in a dilution rack, dispensing solvent into the sample solution in a manner which produces a diluted sample solution, moving the dilution nozzle with said robot into a nozzle washing vessel capable of rinsing the nozzle to rinse the dilution nozzle, grasping with the chuck of the robot a pipetter nozzle connectable to a sampling pipetter with a flexible tube, moving the pipetter nozzle to the sample tube containing the diluted sample solution, pipetting at least a portion of the diluted sample solution with said sampling pipetter into a reaction tube supported in a rack in an incubator, moving the pipetter nozzle into the nozzle washing vessel to rinse the nozzle, grasping with the chuck of the robot a plurality of a reaction mixture nozzles one by one, each nozzle connectable to a reaction mixture dispenser for dispensing a different one of reaction mixture components, moving sequentially with said robot the respective reaction mixture nozzles to the reaction tube, and injecting sequentially the respective reaction mixture components from said reaction mixture dispenser into the reaction tube to produce a reaction mixture, wherein all the steps performed by the robot are automatically controlled by a computer.

22. A method of automatically filtering a reaction mixture, concentrating the filtrate, and injecting the concentrated filtrate into an analysis apparatus, said method comprising:

drawing a reaction mixture contained in a reaction tube through a sampling nozzle operatively connected to a syringe pump;

filtering the reaction mixture in a filtering unit disposed downstream of the sampling nozzle, controlling a first valve connected to a sampling loop and disposed downstream of the filter unit to cause a predetermined volume of filtrate to be received therein from said filtering unit, feeding the filtrate into a concentration column capable of adsorbing the filtrate, feeding an eluting solvent into the concentration column to elute the filtrate adsorbed on the concentration column, and injecting the eluted filtrate into an analytical column capable of analyzing the filtrate, wherein the steps are performed automatically.

* * * * *